US009079916B2

(12) United States Patent
Hadida Ruah et al.

(10) Patent No.: US 9,079,916 B2
(45) Date of Patent: Jul. 14, 2015

(54) HETEROARYL DERIVATIVES AS CFTR MODULATORS

(71) Applicant: Vertex Pharmaceuticals Incorporated, Boston, MA (US)

(72) Inventors: Sara Hadida Ruah, La Jolla, CA (US); Mark Miller, San Diego, CA (US); Jinglan Zhou, San Diego, CA (US); Brian Bear, Carlsbad, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/314,229

(22) Filed: Jun. 25, 2014

(65) Prior Publication Data

US 2014/0371230 A1   Dec. 18, 2014

Related U.S. Application Data

(63) Continuation of application No. 13/627,222, filed on Sep. 26, 2012, now Pat. No. 8,796,312, which is a continuation of application No. 12/392,298, filed on Feb. 25, 2009, now Pat. No. 8,299,099.

(60) Provisional application No. 61/032,159, filed on Feb. 28, 2008.

(51) Int. Cl.
| | |
|---|---|
| *C07D 239/42* | (2006.01) |
| *A61K 31/506* | (2006.01) |
| *C07D 491/048* | (2006.01) |
| *C07D 213/75* | (2006.01) |
| *C07D 241/20* | (2006.01) |
| *A61K 31/443* | (2006.01) |
| *A61K 31/497* | (2006.01) |
| *A61K 31/501* | (2006.01) |
| *A61K 31/513* | (2006.01) |
| *A61K 31/519* | (2006.01) |
| *A61K 45/06* | (2006.01) |
| *C07D 405/12* | (2006.01) |
| *C07D 405/14* | (2006.01) |
| *G01N 33/50* | (2006.01) |

(52) U.S. Cl.
CPC .......... *C07D 491/048* (2013.01); *A61K 31/443* (2013.01); *A61K 31/497* (2013.01); *A61K 31/501* (2013.01); *A61K 31/506* (2013.01); *A61K 31/513* (2013.01); *A61K 31/519* (2013.01); *A61K 45/06* (2013.01); *C07D 213/75* (2013.01); *C07D 239/42* (2013.01); *C07D 241/20* (2013.01); *C07D 405/12* (2013.01); *C07D 405/14* (2013.01); *G01N 33/5008* (2013.01); *G01N 2500/10* (2013.01)

(58) Field of Classification Search
CPC ............. C07D 239/42; C07D 491/048; A61K 31/443; A61K 31/506

USPC .......... 544/250, 312, 321, 328, 329; 514/267, 514/272, 274, 275
See application file for complete search history.

(56) References Cited

U.S. PATENT DOCUMENTS

| | | |
|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Hadida-Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Ruah et al. |
| 8,232,302 B2 | 7/2012 | Miller et al. |
| 8,242,149 B2 | 8/2012 | Hadida-Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida Ruah et al. |
| 8,324,207 B2 | 12/2012 | Hadida-Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor et al. |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel et al. |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |

(Continued)

*Primary Examiner* — Deepak Rao
(74) *Attorney, Agent, or Firm* — Michael J. DiVerdi

(57) ABSTRACT

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

38 Claims, No Drawings

(56) References Cited

U.S. PATENT DOCUMENTS

| | | |
|---|---|---|
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Hadida Ruah et al. |
| 8,524,910 B2 | 9/2013 | Hadida-Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel et al. |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Hadida-Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarzs-Shokri et al. |
| 8,674,108 B2 | 3/2014 | Luisi et al. |
| 8,710,075 B2 | 4/2014 | Binch et al. |
| 8,716,338 B2 | 5/2014 | Young et al. |
| 8,722,704 B2 | 5/2014 | Hadida Ruah et al. |
| 8,741,922 B2 | 6/2014 | Zhang et al. |
| 8,741,925 B2 | 6/2014 | Hadida Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida-Ruah et al. |
| 8,802,700 B2 | 8/2014 | Sheth et al. |
| 8,802,844 B2 | 8/2014 | Gallardo-Godoy et al. |
| 8,802,868 B2 | 8/2014 | Keshavarz-Shokri et al. |
| 8,816,093 B2 | 8/2014 | Siesel et al. |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 2005/0113423 A1 | 5/2005 | VanGoor et al. |
| 2008/0306062 A1 | 12/2008 | Hadida-Ruah et al. |
| 2009/0105272 A1 | 4/2009 | Grootenhuis |
| 2009/0176839 A1 | 7/2009 | Keshavarz-Shokri et al. |
| 2009/0246820 A1 | 10/2009 | Singh et al. |
| 2010/0036130 A1 | 2/2010 | Siesel et al. |
| 2010/0074949 A1 | 3/2010 | Rowe et al. |
| 2010/0125090 A1 | 5/2010 | Hadida-Ruah et al. |
| 2010/0144798 A1 | 6/2010 | VanGoor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Van Goor et al. |
| 2011/0288122 A1 | 11/2011 | Van Goor et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0116238 A1 | 5/2013 | Looker et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0178471 A1 | 7/2013 | Hadida-Ruah et al. |
| 2013/0184276 A1 | 7/2013 | Hadida Ruah et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0237569 A1 | 9/2013 | Hadida-Ruah et al. |
| 2013/0245010 A1 | 9/2013 | Hadida-Ruah et al. |
| 2013/0245011 A1 | 9/2013 | Hadida-Ruah et al. |
| 2013/0303484 A1 | 11/2013 | Grootenhuis et al. |
| 2013/0317020 A1 | 11/2013 | Hadida-Ruah et al. |
| 2013/0324743 A1 | 12/2013 | Belmont et al. |
| 2013/0331567 A1 | 12/2013 | Hadida-Ruah et al. |
| 2014/0023706 A1 | 1/2014 | Verwijs et al. |
| 2014/0024672 A1 | 1/2014 | Hadida-Ruah et al. |
| 2014/0057906 A1 | 2/2014 | Hadida-Ruah et al. |
| 2014/0072995 A1 | 3/2014 | Hadida-Ruah et al. |
| 2014/0073653 A1 | 3/2014 | Binch et al. |
| 2014/0080825 A1 | 3/2014 | Hadida-Ruah et al. |
| 2014/0080826 A1 | 3/2014 | Ruah et al. |
| 2014/0088141 A1 | 3/2014 | Binch et al. |
| 2014/0088160 A1 | 3/2014 | Alargova et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0121379 A1 | 5/2014 | Siesel et al. |
| 2014/0121381 A1 | 5/2014 | Hadida-Ruah et al. |
| 2014/0142138 A1 | 5/2014 | Van Goor et al. |
| 2014/0142312 A1 | 5/2014 | Luisi et al. |
| 2014/0155431 A1 | 6/2014 | Hadida Ruah et al. |
| 2014/0155626 A1 | 6/2014 | Hadida-Ruah et al. |
| 2014/0163011 A1 | 6/2014 | Hadida Ruah et al. |
| 2014/0163068 A1 | 6/2014 | Verwijs et al. |
| 2014/0187787 A1 | 7/2014 | Ambhaikar et al. |
| 2014/0206689 A1 | 7/2014 | Hadida Ruah et al. |
| 2014/0206720 A1 | 7/2014 | Young et al. |
| 2014/0221424 A1 | 8/2014 | Zha et al. |
| 2014/0221430 A1 | 8/2014 | Keshavaraz-Shokri et al. |
| 2014/0235625 A1 | 8/2014 | Binch et al. |
| 2014/0235668 A1 | 8/2014 | Binch et al. |
| 2014/0242172 A1 | 8/2014 | Hurter et al. |
| 2014/0243289 A1 | 8/2014 | Grootenhuis et al. |
| 2014/0255483 A1 | 9/2014 | Dokou et al. |
| 2014/0256770 A1 | 9/2014 | DeMattei et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |

HETEROARYL DERIVATIVES AS CFTR MODULATORS

CROSS REFERENCE TO RELATED APPLICATIONS

This application is a continuation of U.S. patent application Ser. No. 13/627,222, filed Sep. 26, 2012, which is a continuation of U.S. patent application Ser. No. 12/392,298, filed Feb. 25, 2009 which in turn claims the benefit of priority under 35 U.S.C. § 119 to U.S. provisional patent application Ser. No. 61/032,159, filed Feb. 28, 2008, the entire contents of each of which are incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeate of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genetsickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the endoplasmic reticulum ("ER"), and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$-$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$-$K^+$-ATPase pump and Cl— channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include *cryptosporidium, giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity, particularly CFTR activity. These compounds have the general formula I:

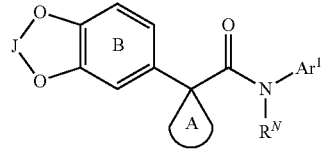

or a pharmaceutically acceptable salt thereof, wherein $Ar^1$, $R^N$, ring A, ring B, and J are described below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (di), neurophyseal di, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjögren's disease.

DETAILED DESCRIPTION OF THE INVENTION

General Description of Compounds of the Invention

The present invention relates to compounds of formula I:

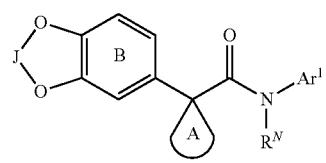

or a pharmaceutically acceptable salt thereof, wherein:
$Ar^1$ is:

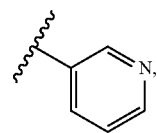

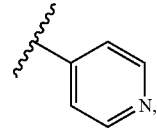

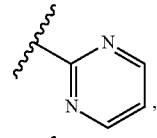

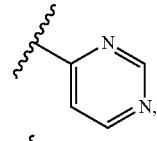

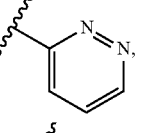 or

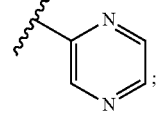

$Ar^1$ is optionally substituted with w occurrences of —W—$R^W$; wherein

W is independently a bond or an optionally substituted (C1-C6) alkylidene chain wherein up to two methylene units of W are independently replaced by —CO—, —O—, —S—, —$SO_2$—, or —NR'—;

R' is independently H, alkyl, aryl, heteroaryl, aralkyl, cycloalkyl, or heterocycloalkyl; and $R^W$ is independently H, halo, CN, $NO_2$, $NH_2$, $CF_3$, $OCF_3$, OH, alkoxy, or an optionally substituted aliphatic, cycloalkyl, heterocycloalkyl, aryl, or heteroaryl, wherein, when substituted, $R^w$ is substituted with up to two $R^2$;

$R^2$ is halo, CN, $NO_2$, $CF_3$, $OCF_3$, OR, —(C1-C6)alkylidene-OH, —(C1-C6)alkylidene-N(R)$_2$, OC(O)R, OC(O)N(R)$_2$, SR, S(O)R, $SO_2$R, $SO_2$N(R)$_2$, $SO_3$R, C(O)R, $CO_2$R, C(O)N(R)$_2$, N(R)$_2$, NRC(O)R, $NRCO_2$R, NRC(O)N(R)$_2$, $NRSO_2$R, B(OR)$_2$, or $NRSO_2$N(R)$_2$;

R is independently H, alkyl, cycloalkyl, heterocyclic, aryl, or heteroaryl;

$R^N$ is H, alkyl, aryl, heteroaryl, aralkyl, cycloalkyl, or heterocycloalkyl;

A is an optionally substituted 3-7 membered monocyclic ring;

B is optionally fused to a 5-7 membered ring selected from the group consisting of cycloaliphatic, aryl, heterocyclic, and heteroaryl;

J is selected from the group consisting of $CH_2$, $CF_2$, $C(CH_3)_2$, C(O),

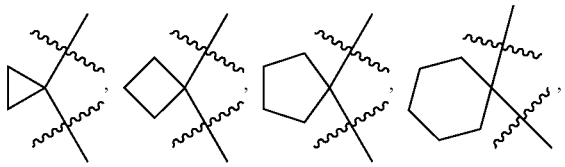

C(Phenyl)$_2$, B(OH), and CH(OEt); and w is an integer from 0 to 4 inclusive;

provided that when $Ar^1$ is

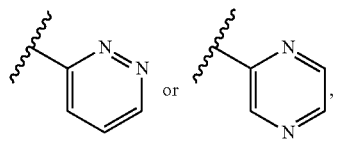 [SMILES: *c1cccnn1 ; *c1cnccn1]

W is independently an optionally substituted (C1-C6) alkylidene chain wherein up to two methylene units of W are independently replaced by —CO—, —O—, —S—, —$SO_2$—, or —NR'—.

Compounds and Definitions:

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycloalkyl", "heterocyclyl", "heterocycloaliphatic", or "heterocyclic" groups.

The term "heterocycloalkyl", "heterocyclyl", "heterocycloaliphatic", or "heterocyclic" as used herein means non-aromatic, monocyclic, bicyclic, or tricyclic ring systems in which one or a plurality of ring members is an independently selected heteroatom. In some embodiments, the "heterocycloalkyl", "heterocyclyl", "heterocycloaliphatic", or "heterocyclic" group has three to fourteen ring members in which one or more ring members is a heteroatom independently selected from the group consisting of oxygen, sulfur, nitrogen, and phosphorus, and each ring in the system contains 3 to 7 ring members.

The term "heteroatom" means one or more of boron, oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halogen atoms. The term "halogen" means F, Cl, Br, or I. Examples of haloaliphatic include —CHF$_2$, —CH$_2$F, —CF$_3$, —CF$_2$—, or perhaloalkyl, such as, —CF$_2$CF$_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from the group consisting of halogen; —R$^o$; —OR$^o$; —SR$^o$; 1,2-methylene-dioxy; 1,2-ethylenedioxy; phenyl (Ph) optionally substituted with R$^o$; —O(Ph) optionally substituted with R$^o$; —(CH$_2$)$_{1-2}$(Ph), optionally substituted with R$^o$; —CH═CH(Ph), optionally substituted with R$^o$; —NO$_2$; —CN; —N(R$^o$)$_2$; —NR$^o$C(O)R$^o$; —NR$^o$C(O)N(R$^o$)$_2$; —NR$^o$CO$_2$R$^o$; —NR$^o$NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$;—CO$_2$R$^o$;—C(O)R$^o$; —C(O)N(R$^o$)$_2$; —OC(O)N(R$^o$)$_2$; —S(O)$_2$R$^o$; —SO$_2$N(R$^o$)$_2$; —S(O)R$^o$; —NR$^o$SO$_2$N(R$^o$)$_2$; —NR$^o$SO$_2$R$^o$; —C(═S)N(R$^o$)$_2$; —C(═NH)—N(R$^o$)$_2$; and —(CH$_2$)$_{0-2}$NHC(O)R$^o$ wherein each independent occurrence of R$^o$ is selected from the group consisting of hydrogen, optionally substituted C$_{1-6}$ aliphatic, an unsubstituted 5-6 membered heteroaryl or heterocyclic ring, phenyl, —O(Ph), and —CH$_2$(Ph), or, notwithstanding the definition above, two independent occurrences of R$^o$, on the same substituent or different substituents, taken together with the atom(s) to which each R$^o$ group is bound, form a 3-8-membered cycloalkyl, heterocyclyl, aryl, or heteroaryl ring having 0-3 heteroatoms independently selected from the group consisting of nitrogen, oxygen, and sulfur. Optional substituents on the aliphatic group of R$^o$ are selected from the group consisting of NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), and haloC$_{1-4}$aliphatic, wherein each of the foregoing C$_{1-4}$aliphatic groups of R$^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from the group consisting of those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), and ═NR*, where each R* is independently selected from the group consisting of hydrogen and an optionally substituted C$_{1-6}$ aliphatic. Optional substituents on the aliphatic group of R* are selected from the group consisting of NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), and halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from the group consisting of —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(═S)N(R$^+$)$_2$, —C(═NH)—N(R$^+$)$_2$, and —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH═CH(Ph); or an unsubstituted 5-6 membered heteroaryl or heterocyclic ring having one to four heteroatoms independently selected from the group consisting of oxygen, nitrogen, and sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from the group consisting of nitrogen, oxygen, and sulfur. Optional substituents on the aliphatic group or the phenyl ring of R$^+$ are selected from the group consisting of NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), and halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

As detailed above, in some embodiments, two independent occurrences of R$^o$ (or R$^+$, or any other variable similarly defined herein), are taken together with the atom(s) to which each variable is bound to form a 3-8-membered cycloalkyl, heterocyclyl, aryl, or heteroaryl ring having 0-3 heteroatoms independently selected from the group consisting of nitrogen, oxygen, and sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of

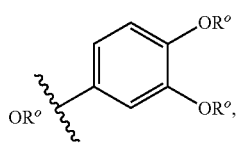

these two occurrences of $R^o$ are taken together with the oxygen atoms to which they are bound to form a fused 6-membered oxygen containing ring:

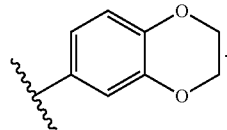 [SMILES: *c1ccc2c(c1)OCCO2]

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Description of Exemplary Compounds:

In one embodiment, the present invention relates to compounds of formula I:

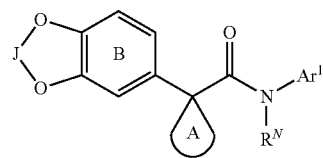

or a pharmaceutically acceptable salt thereof, wherein:
$Ar^1$ is:

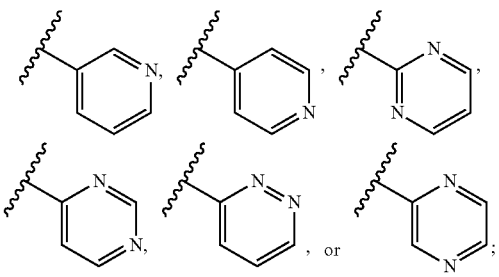

$Ar^1$ is optionally substituted with w occurrences of —W—$R^W$; wherein

W is independently a bond or an optionally substituted (C1-C6) alkylidene chain wherein up to two methylene units of W are independently replaced by —CO—, —O—, —S—, —$SO_2$—, or —NR'—;

R' is independently H, alkyl, aryl, heteroaryl, aralkyl, cycloalkyl, or heterocycloalkyl; and $R^W$ is independently H, halo, CN, $NO_2$, $NH_2$, $CF_3$, $OCF_3$, OH, alkoxy, or an optionally substituted aliphatic, cycloalkyl, heterocycloalkyl, aryl, or heteroaryl, wherein, when substituted, $R^w$ is substituted with up to two $R^2$;

$R^2$ is halo, CN, $NO_2$, $CF_3$, $OCF_3$, OR, —(C1-C6)alkylidene-OH, —(C1-C6)alkylidene-N(R)$_2$, OC(O)R, OC(O)N(R)$_2$, SR, S(O)R, $SO_2R$, $SO_2N(R)_2$, $SO_3R$, C(O)R, $CO_2R$, C(O)N(R)$_2$, N(R)$_2$, NRC(O)R, $NRCO_2R$, NRC(O)N(R)$_2$, $NRSO_2R$, B(OH)$_2$, or $NRSO_2N(R)_2$;

R is independently H, alkyl, cycloalkyl, heterocyclic, aryl, or heteroaryl;

$R^N$ is H, alkyl, aryl, heteroaryl, aralkyl, cycloalkyl, or heterocycloalkyl;

A is an optionally substituted 3-7 membered monocyclic ring;

B is optionally fused to a 5-7 membered ring selected from the group consisting of cycloaliphatic, aryl, heterocyclic, and heteroaryl;

J is selected from the group consisting of $CH_2$, $CF_2$, $C(CH_3)_2$, C(O),

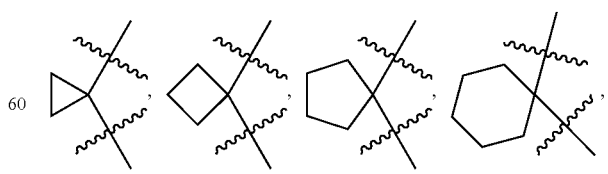

C(Phenyl)$_2$, B(OH), and CH(OEt); and
w is an integer from 0 to 4 inclusive;
provided that when $Ar^1$ is

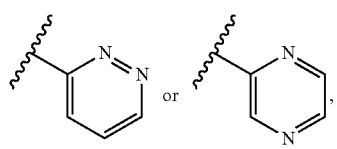 [SMILES: *c1cccnn1 ; *c1cnccn1] or 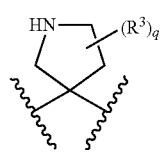,
W is independently an optionally substituted (C1-C6) alkylidene chain wherein up to two methylene units of W are independently replaced by —CO—, —O—, —S—, —SO$_2$—, or —NR'—.
In another embodiment, the present invention relates to compounds of formula I and the attendant definitions, wherein A is selected from the group consisting of:
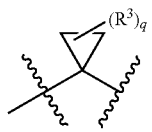
a
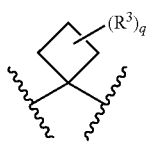
b
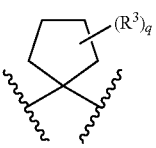
c
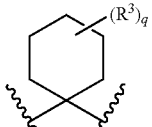
d
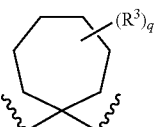
e
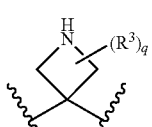
e
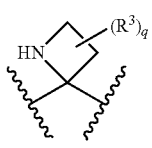
f
-continued
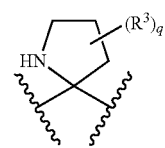
g
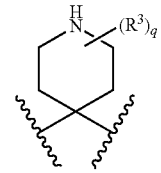
h
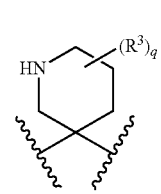
i
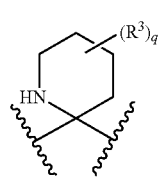
j
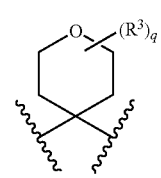
k
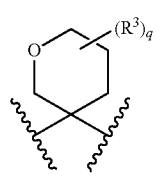
l
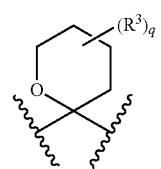
m
n
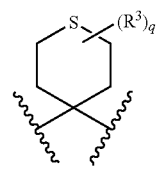
o -continued

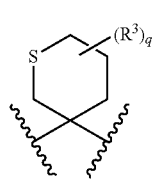 p

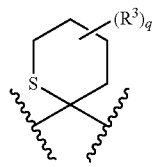 q

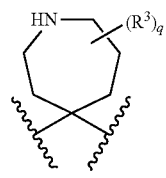 r

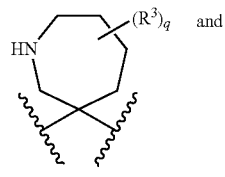 and

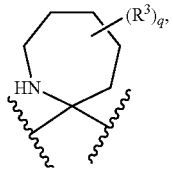

wherein
R³ is alkyl, alkaryl, aryl, or heteroaryl; and q is an integer from 0 to 4 inclusive. In another embodiment, A is

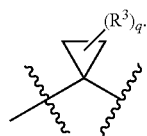

In another embodiment, A is

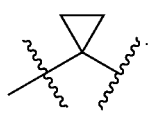 [SMILES: *C1(*)CC1]

In another embodiment, the present invention relates to compounds of formula I and the attendant definitions, wherein J is CH₂. In another embodiment, J is CF₂.

In another embodiment, the present invention relates to compounds of formula I and the attendant definitions, wherein $R^N$ is H, aryl, or heteroaryl. In another embodiment, $R^N$ is H or heteroaryl. In another embodiment, $R^N$ is heteroaryl. In another embodiment, $R^N$ is H.

In another embodiment, the present invention relates to compounds of formula I and the attendant definitions, wherein Ar¹ is fused to a 5-7 membered monocyclic ring or 9-11 bicyclic ring selected from the group consisting of cycloaliphatic, aryl, heterocyclic, and heteroaryl.

In another embodiment, the present invention relates to compounds of formula I and the attendant definitions, wherein optionally substituted Ar¹ is

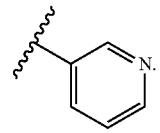 [SMILES: *c1cccnc1]

In another embodiment, optionally substituted Ar¹ is

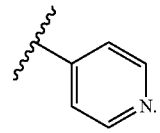 [SMILES: *c1ccncc1]

In another embodiment, optionally substituted Ar¹ is

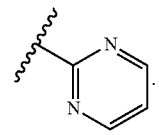

In another embodiment, optionally substituted Ar¹ is

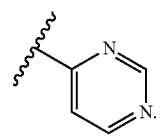

In another embodiment, optionally substituted Ar¹ is

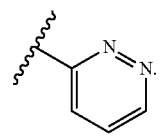

In another embodiment, optionally substituted Ar¹ is

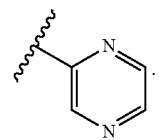

In another embodiment, the present invention relates to compounds of formula I and the attendant definitions, wherein w is 0. In another embodiment, w is 1. In another embodiment, w is 2.

In another embodiment, the present invention relates to compounds of formula I and the attendant definitions, wherein W is a bond. In another embodiment, W is an optionally substituted (C1-C6) alkylidene chain. In another embodiment, W is —CH$_2$—. In another embodiment, W is —NH—. In another embodiment, W is —O—. In another embodiment, W is —SO$_2$—.

In another embodiment, the present invention relates to compounds of formula I and the attendant definitions, wherein R$^w$ is H. In another embodiment, R$^w$ is OH. In another embodiment, R$^w$ is aryl. In another embodiment, R$^w$ is phenyl. In another embodiment, R$^w$ is heteroaryl. In another embodiment, R$^w$ is pyridyl. In another embodiment, R$^w$ is alkoxy. In another embodiment, R$^w$ is methoxy. In another embodiment, R$^w$ is trifluoromethoxy. In another embodiment, R$^w$ is cycloalkyl. In another embodiment, R$^w$ is cyclohexyl. In another embodiment, R$^w$ is heterocycloalkyl. In another embodiment, R$^w$ is unsaturated heterocycloalkyl. In another embodiment, R$^w$ is pyridone. In another embodiment, R$^w$ is —(C1-C6)alkylidene-N(R)$_2$. In another embodiment, R$^w$ is —(C1-C6)alkylidene-OH. In another embodiment, R$^w$ is —CH$_2$OH.

In another embodiment, the present invention relates to compounds of formula I and the attendant definitions, wherein Ar$^1$ is substituted with an acyclic —W—R$^w$.

In another embodiment, the present invention relates to compounds of formula I and the attendant definitions, wherein Ar$^1$ is substituted with —W—R$^w$ that is an aryl, heteroaryl, or cycloalkyl.

In another embodiment, the present invention relates to compounds of formula I and the attendant definitions, wherein Ar$^1$ is substituted with at least one —W—R$^w$ having the formula

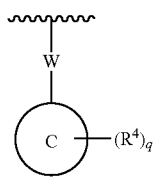

wherein,

W is a straight chain or branched (C1-C6)alkylidene, wherein a methylene group may be replaced with —O—, —SO$_2$—, or —NR'—;

R' is H or alkyl;

C is aryl or heteroaryl;

R$^4$ is halo, —(C1-C6)alkyl, CN, NO$_2$, CF$_3$, OCF$_3$, OR, —(C1-C6)alkylidene-OH, SO$_2$N(R)$_2$, NRSO$_2$R, C(O)R, CO$_2$R, C(O)N(R)$_2$, N(R)$_2$, or NRC(O)R; and q is an integer from 0 to 5 inclusive.

In another embodiment, Ar$^1$ is substituted with at least one —W—R$^w$ selected from the following:

—OH, —CH$_3$, —OMe, —CN, —CF$_3$,

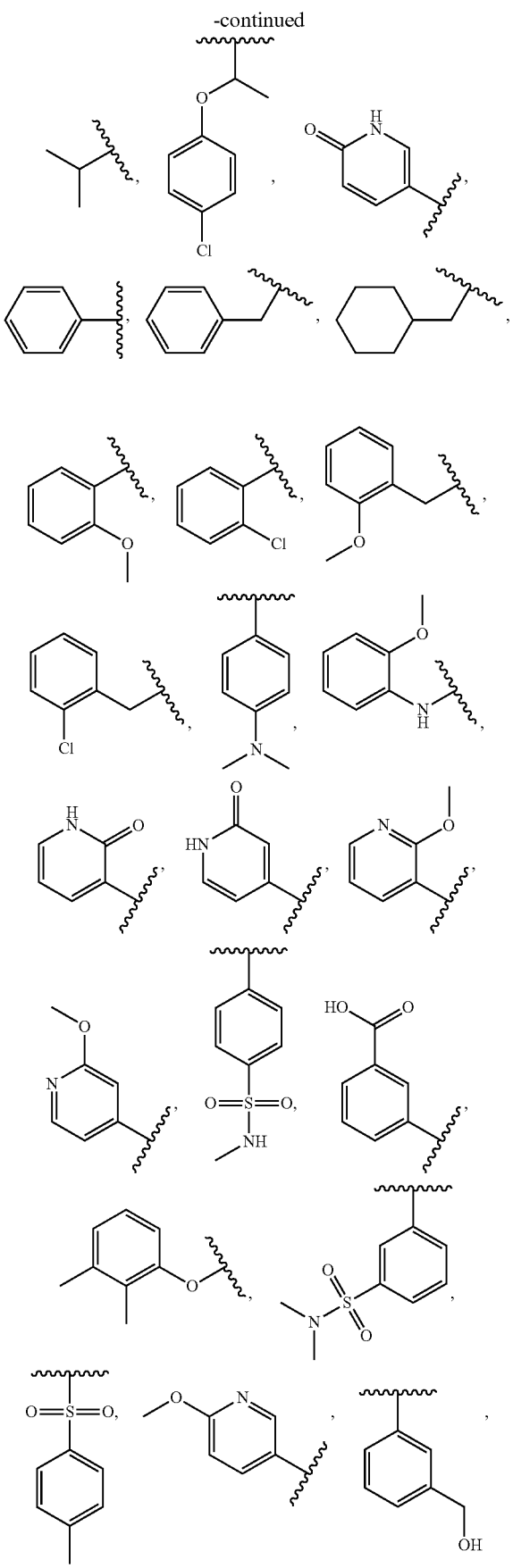

-continued

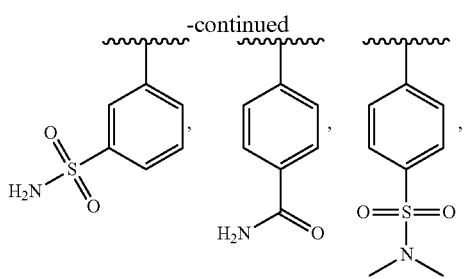

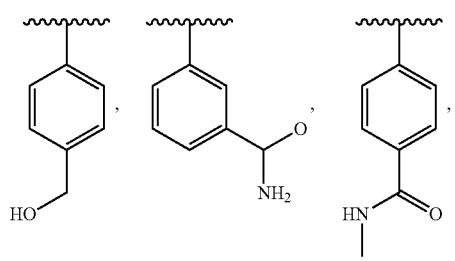

In another embodiment, the present invention relates to a compound of formula I and the attendant definitions, wherein Ar¹ is substituted with at least one —W—R^w selected from the following:

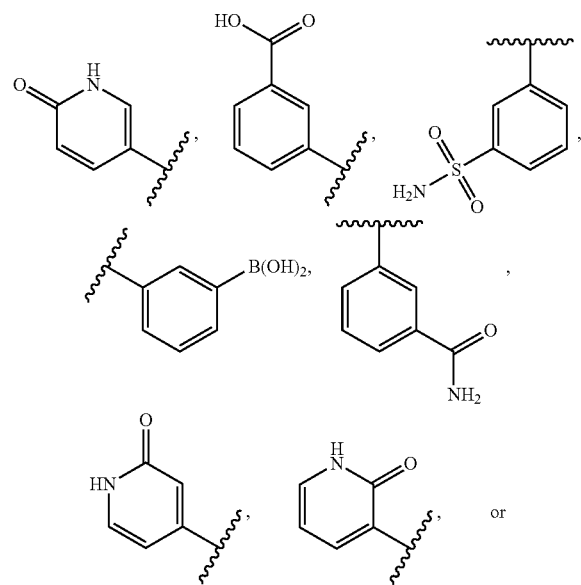

-continued

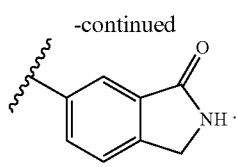

In another embodiment, the present invention relates to compounds having formula Ia:

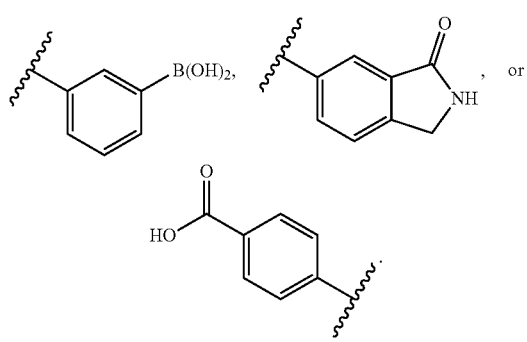

wherein:
J is $CH_2$ or $CF_2$;
$R^N$ is H, alkyl, aryl, or heteroaryl;
Ar¹ is

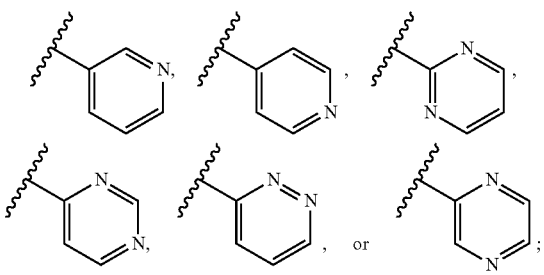

Ar¹ is optionally substituted with w occurrences of —W—$R^W$; wherein
W is independently a bond or an optionally substituted (C1-C6) alkylidene chain wherein up to two methylene units of W are independently replaced by —O—, —$SO_2$—, or —NR'—;
R' is independently H, alkyl, or aryl; and
$R^W$ is independently H, halo, CN, $CF_3$, OH, alkoxy, or an optionally substituted aliphatic, cycloalkyl, heterocycloalkyl, aryl, or heteroaryl, wherein, when substituted, $R^w$ is substituted with up to two $R^2$;
$R^2$ is halo, $CF_3$, OR, —(C1-C6)alkylidene-OH, $SO_2N(R)_2$, $CO_2R$, $C(O)N(R)_2$, $B(OH)_2$, or $N(R)_2$;
R is independently H, alkyl, cycloalkyl, heterocyclic, aryl, or heteroaryl; and
w is an integer from 0 to 4 inclusive;
provided that when Ar¹ is

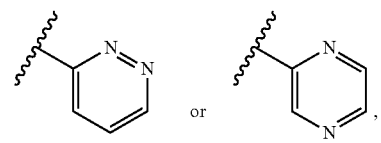 [SMILES: *c1cccnn1 ; *c1cnccn1]

W is independently an optionally substituted (C1-C6) alkylidene chain wherein up to two methylene units of W are independently replaced by —CO—, —O—, —S—, —$SO_2$—, or —NR'—.

In another embodiment, the present invention relates to compounds of formula Ia and the attendant definitions, wherein J is CH$_2$. In another embodiment, J is CF$_2$.

In another embodiment, the present invention relates to compounds of formula Ia and the attendant definitions, wherein R$^N$ is H or heteroaryl. In another embodiment, R$^N$ is heteroaryl. In another embodiment, R$^N$ is H.

In another embodiment, Ar$^1$ is selected from the following:

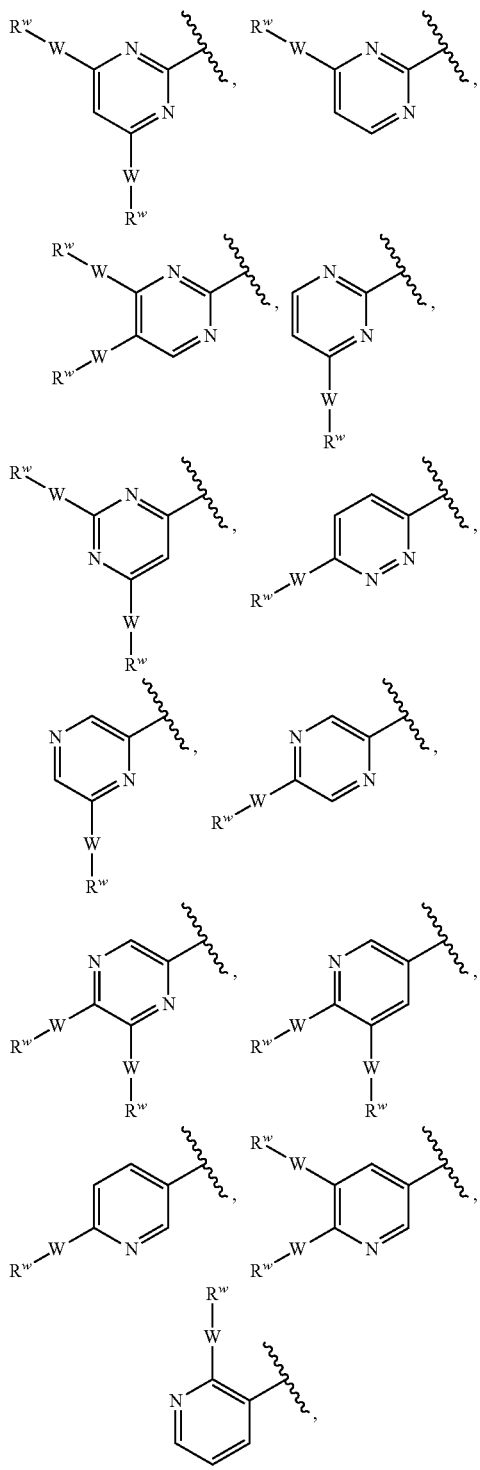

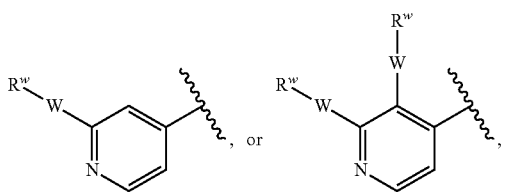

In another embodiment, the present invention relates to compounds of formula Ia and the attendant definitions, wherein Ar$^1$ is substituted with an acyclic —W—R$^w$.

In another embodiment, the present invention relates to compounds of formula Ia and the attendant definitions, wherein Ar$^1$ is substituted with —W—R$^w$ that is an aryl, heteroaryl, or cycloalkyl ring. In another embodiment, the present invention relates to compounds of formula Ia and the attendant definitions, wherein Ar$^1$ is substituted with —W—R$^w$ that is an unsaturated heterocycloalkyl. In a further embodiment, —W—R$^w$ is a pyridone.

In another embodiment, the present invention relates to compounds of formula Ia and the attendant definitions, wherein Ar$^1$ is substituted with at least one —W—R$^w$ selected from the following:

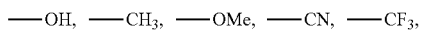

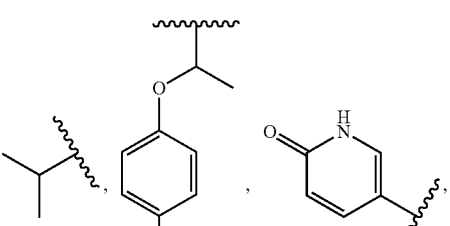

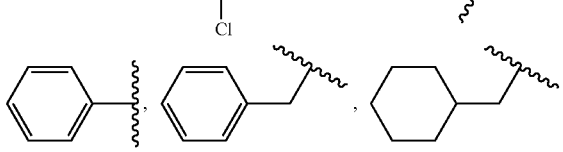

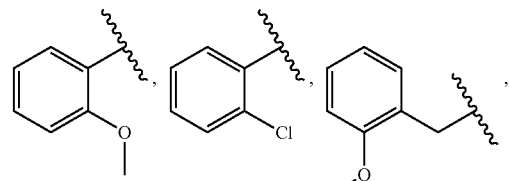

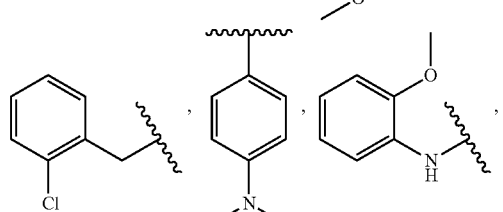

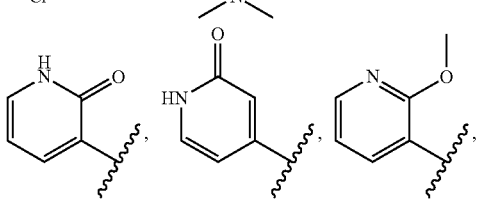

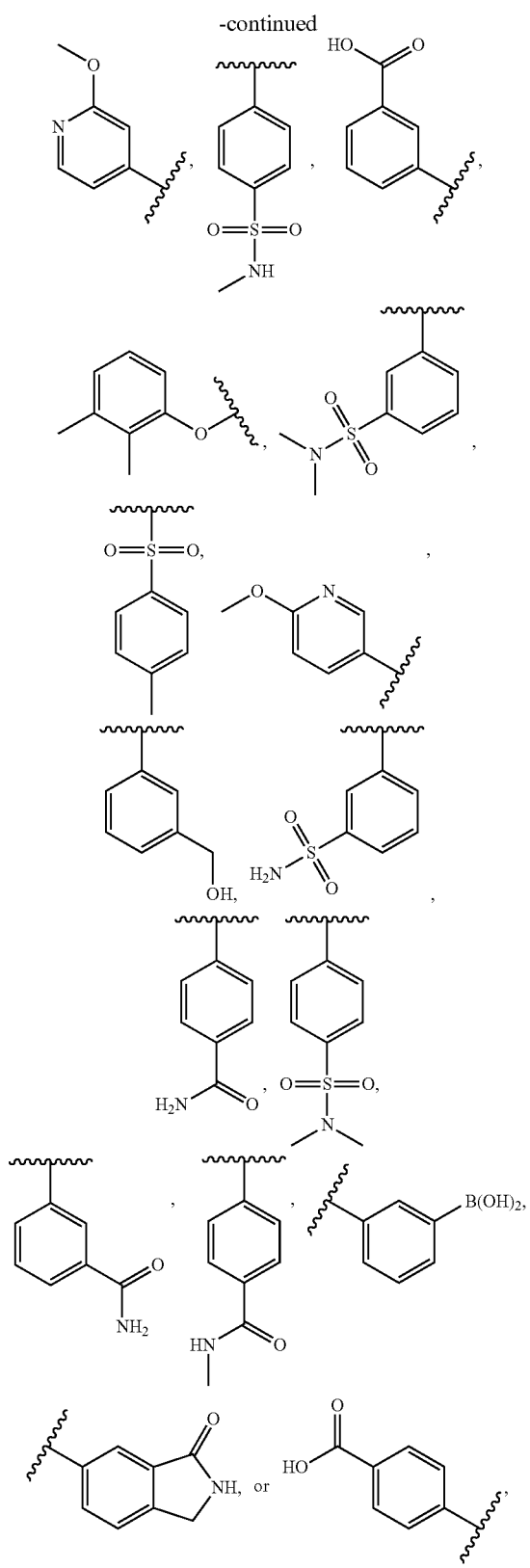
In another embodiment, the present invention relates to a compound of formula Ia and the attendant definitions, wherein $Ar^1$ is substituted with at least one —W—$R^w$ selected from the following:
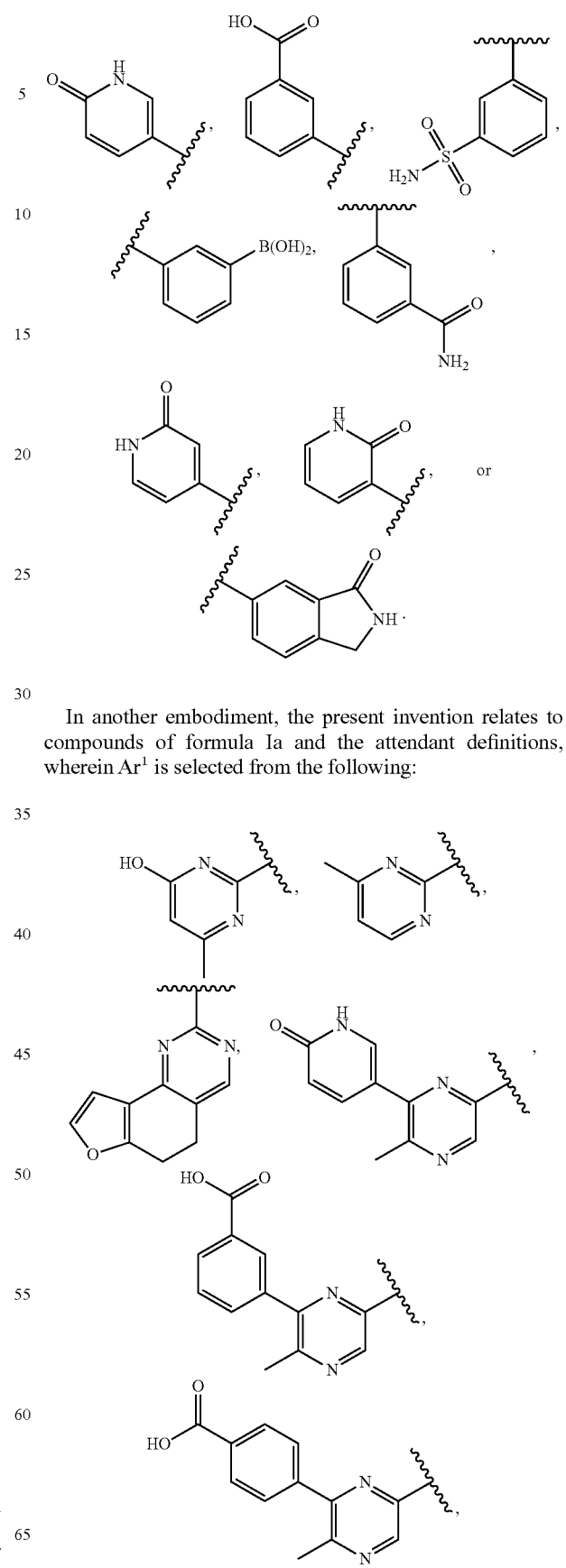
In another embodiment, the present invention relates to compounds of formula Ia and the attendant definitions, wherein $Ar^1$ is selected from the following:

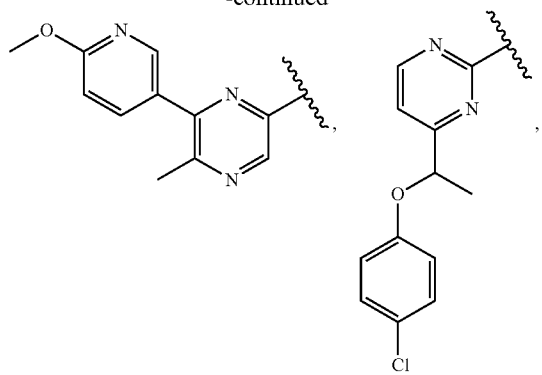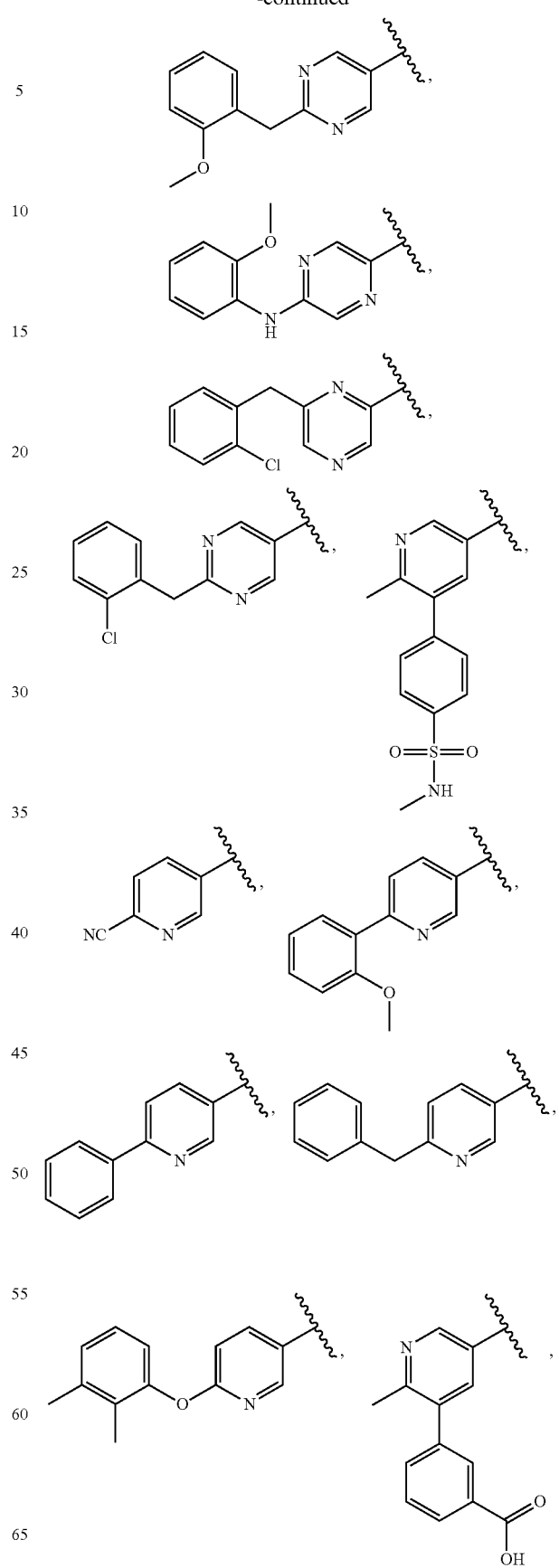

-continued
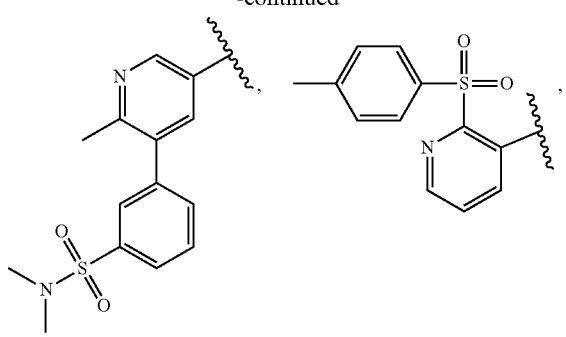 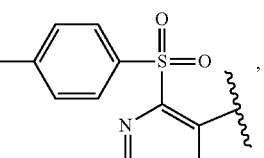 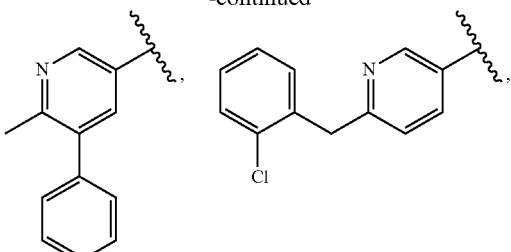 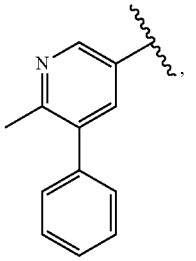
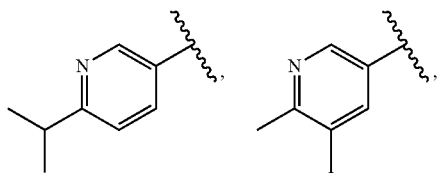 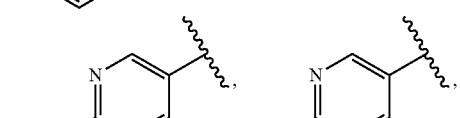 
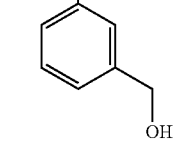 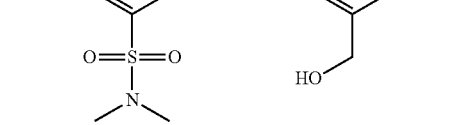
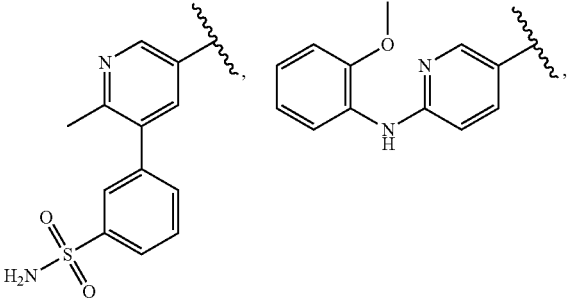 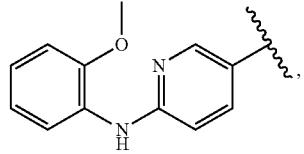 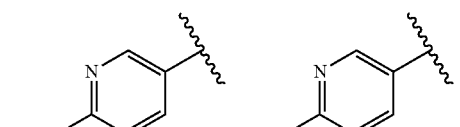 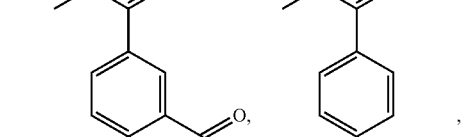
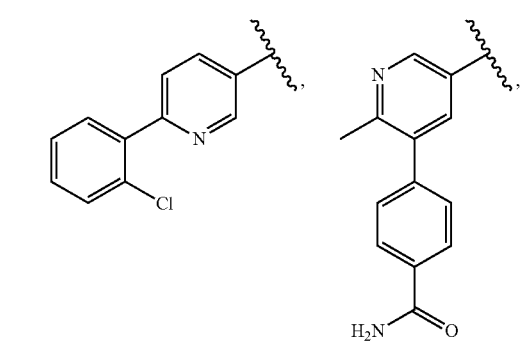 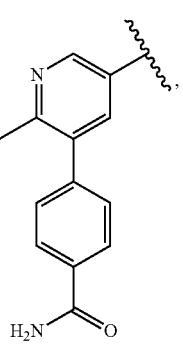 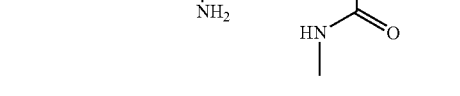
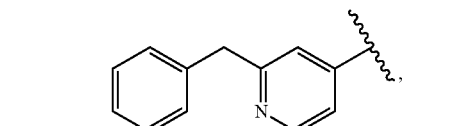
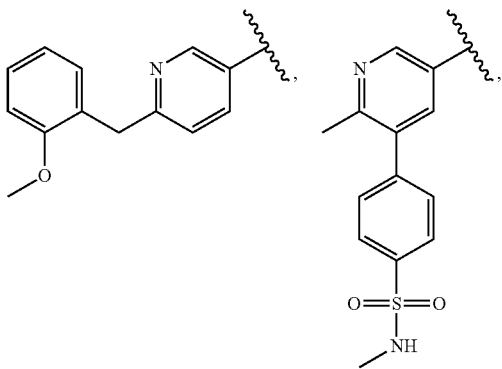 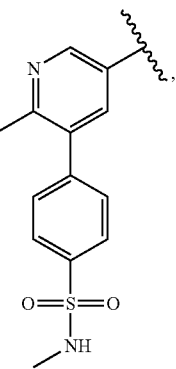 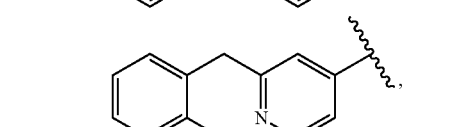
or
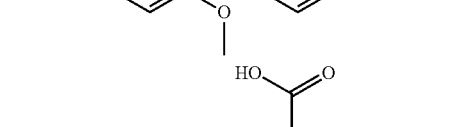

In another embodiment, the present invention relates to compounds having formula Ib:
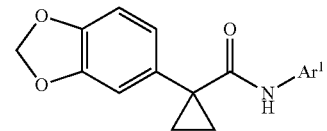
Ib
or a pharmaceutically acceptable salt thereof, wherein:
Ar¹ is selected from the following:
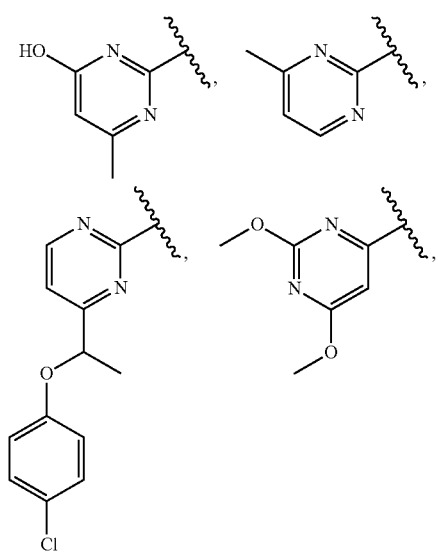
-continued
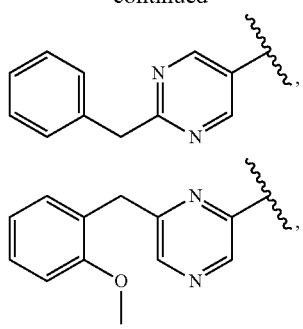
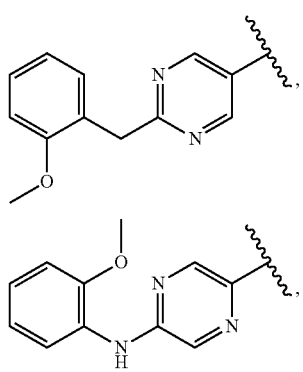
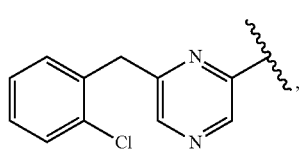
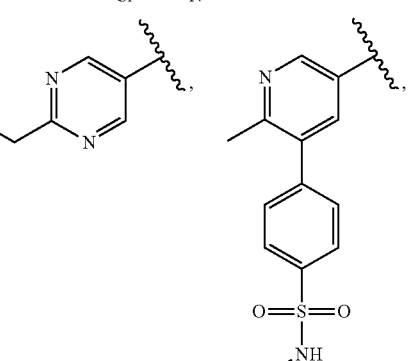
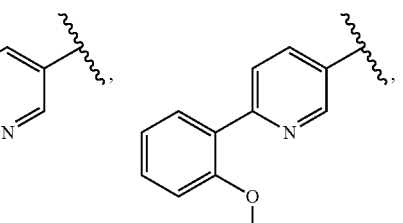
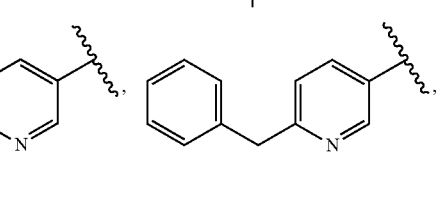

-continued
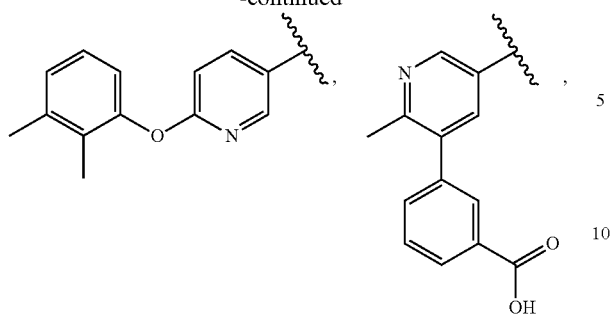
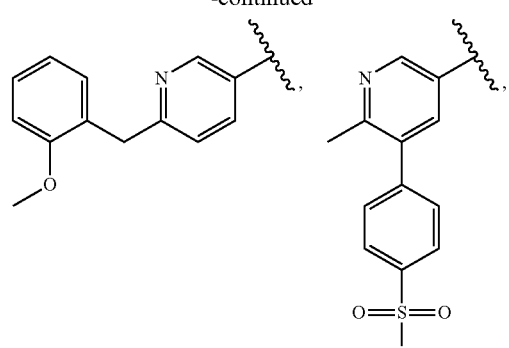
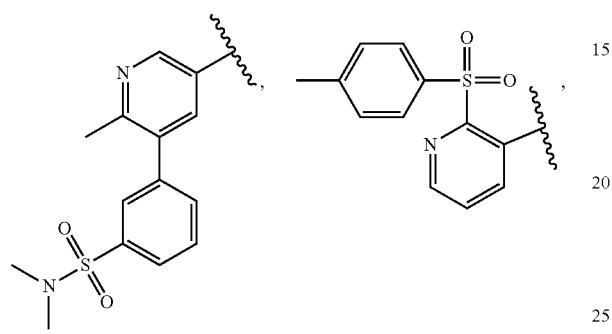
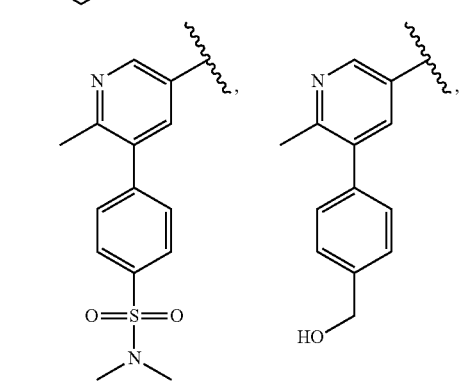
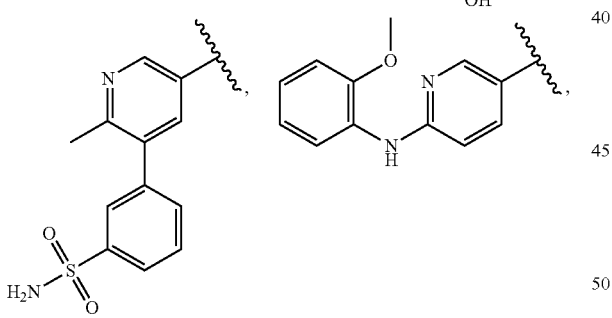
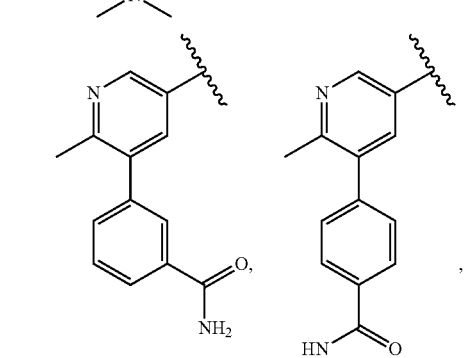
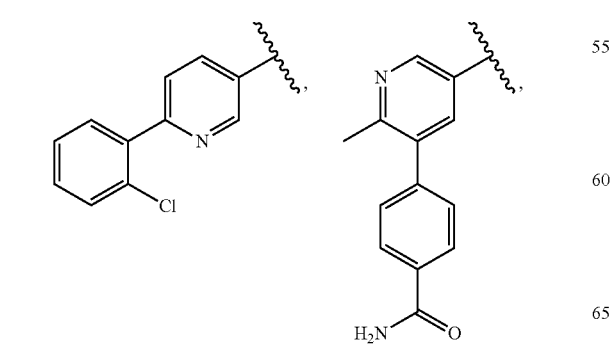
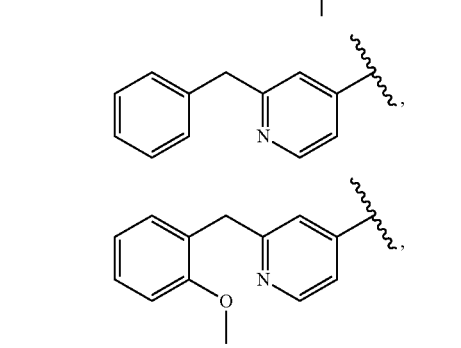

-continued
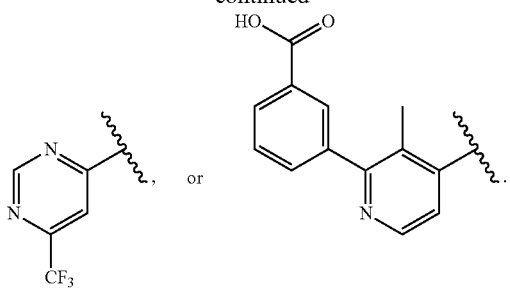
or
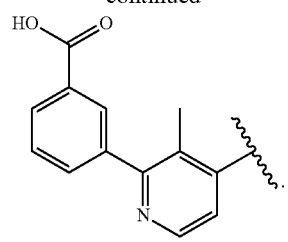
In another embodiment, the present invention relates to compounds having formula Ic:
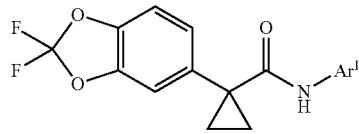
Ic
or a pharmaceutically acceptable salt thereof, wherein:
Ar¹ is selected from the following:
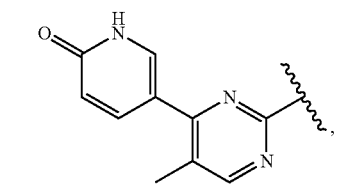
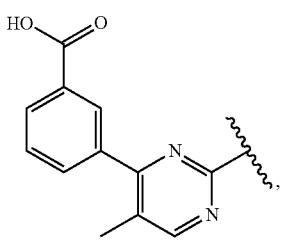
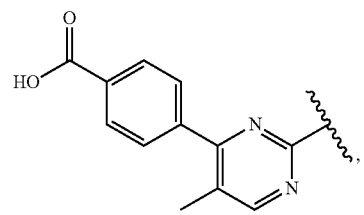
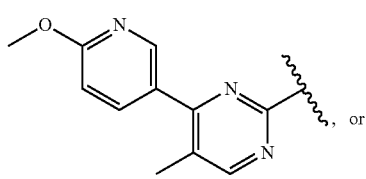
In another embodiment, the present invention relates to an exemplary compound selected from Table 1.
TABLE 1

TABLE 1-continued
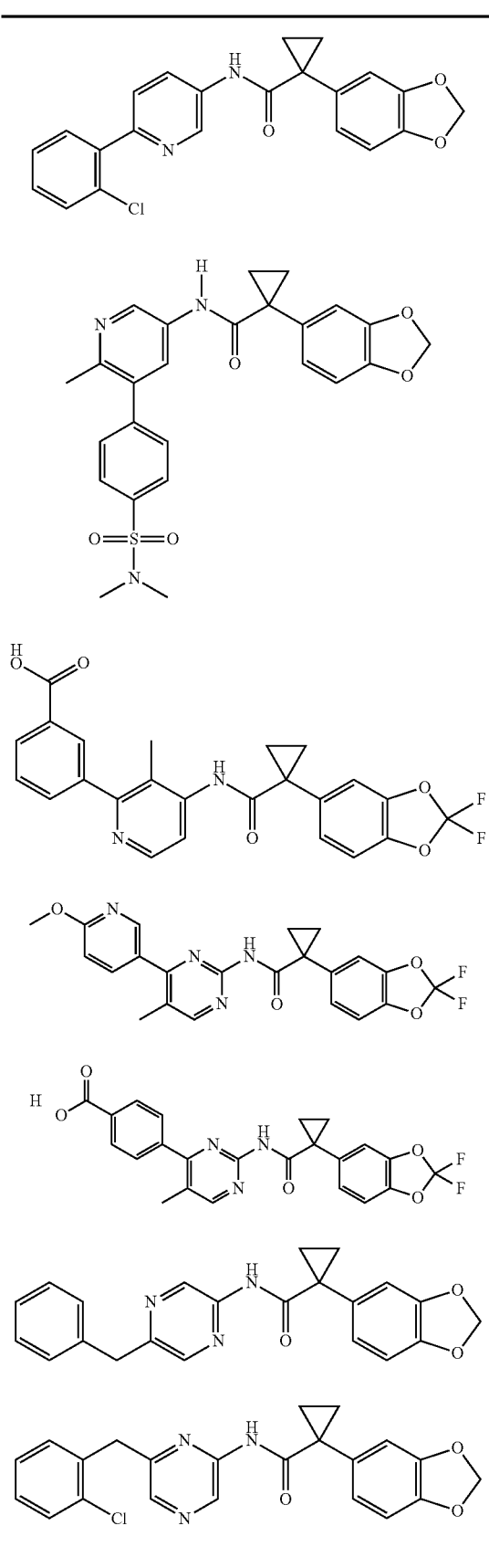
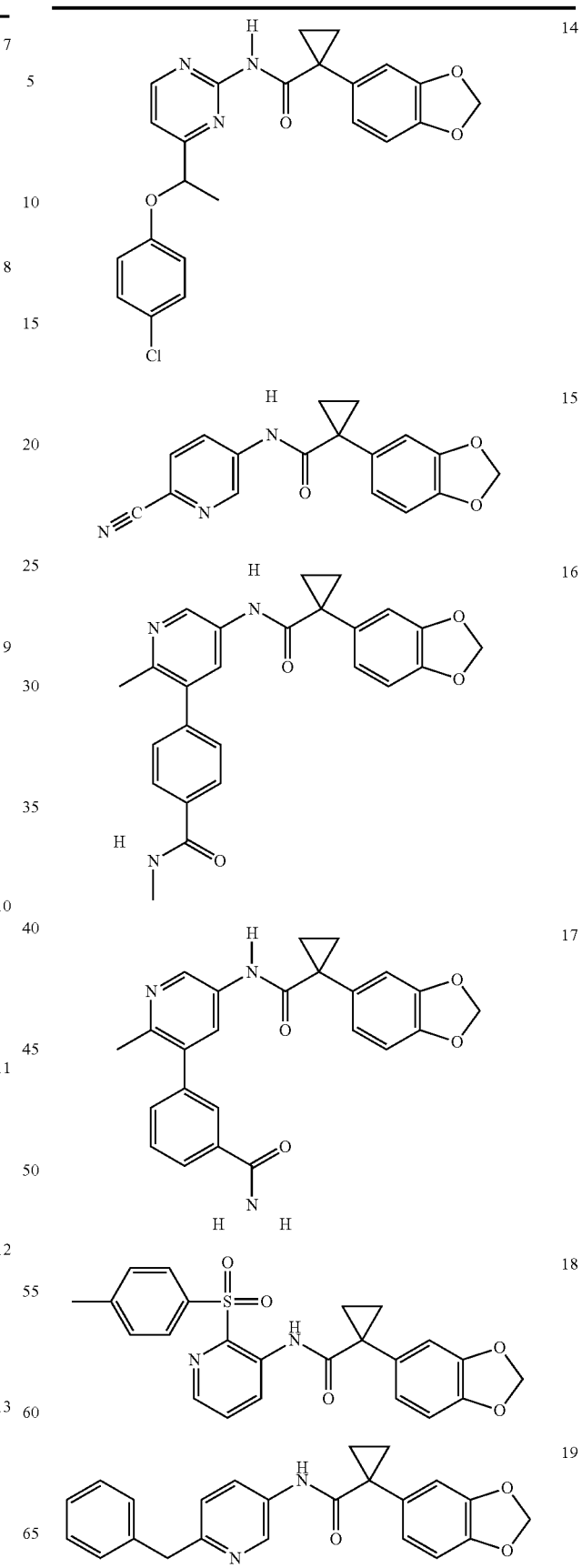

TABLE 1-continued
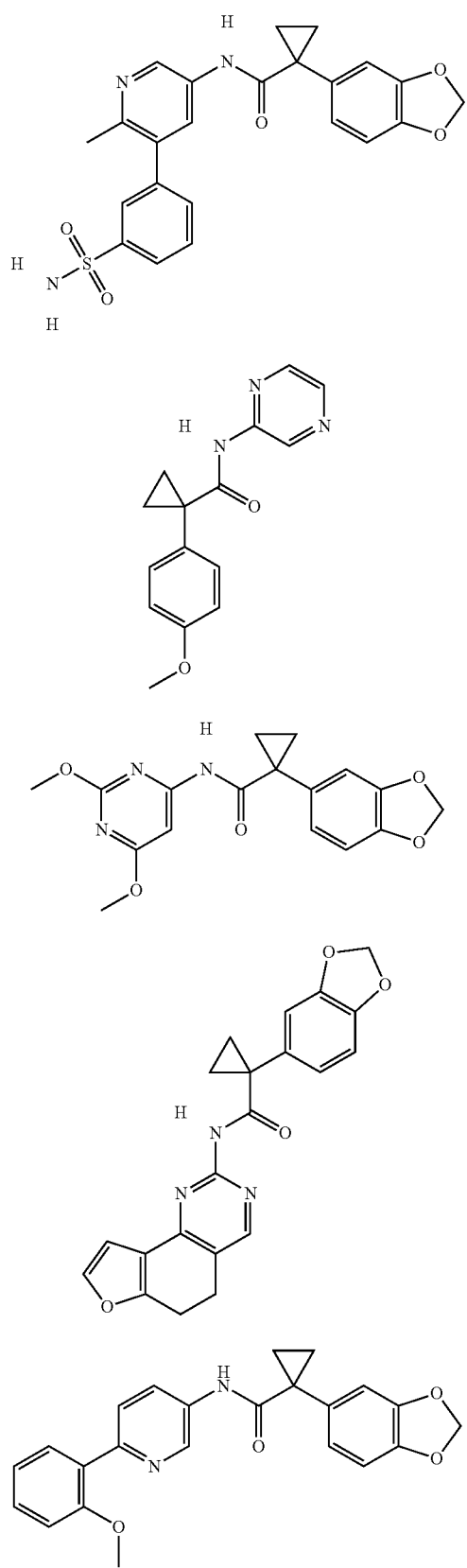
TABLE 1-continued
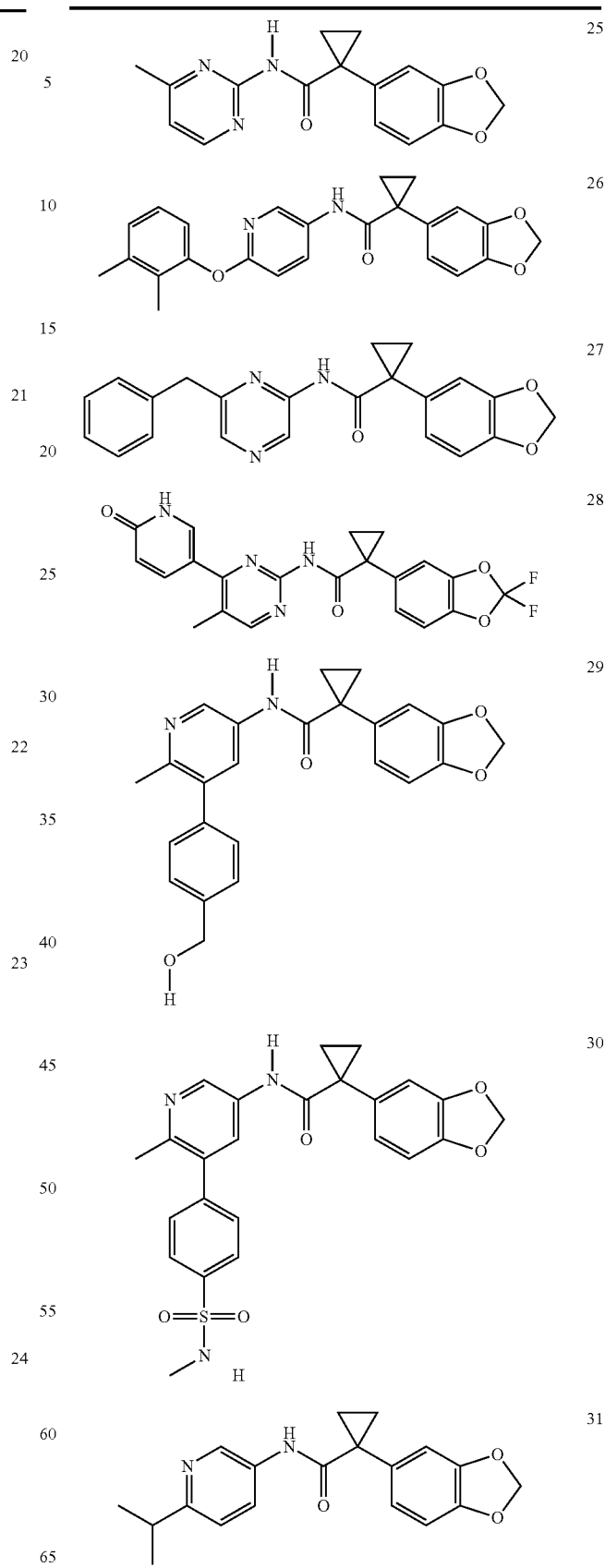

TABLE 1-continued
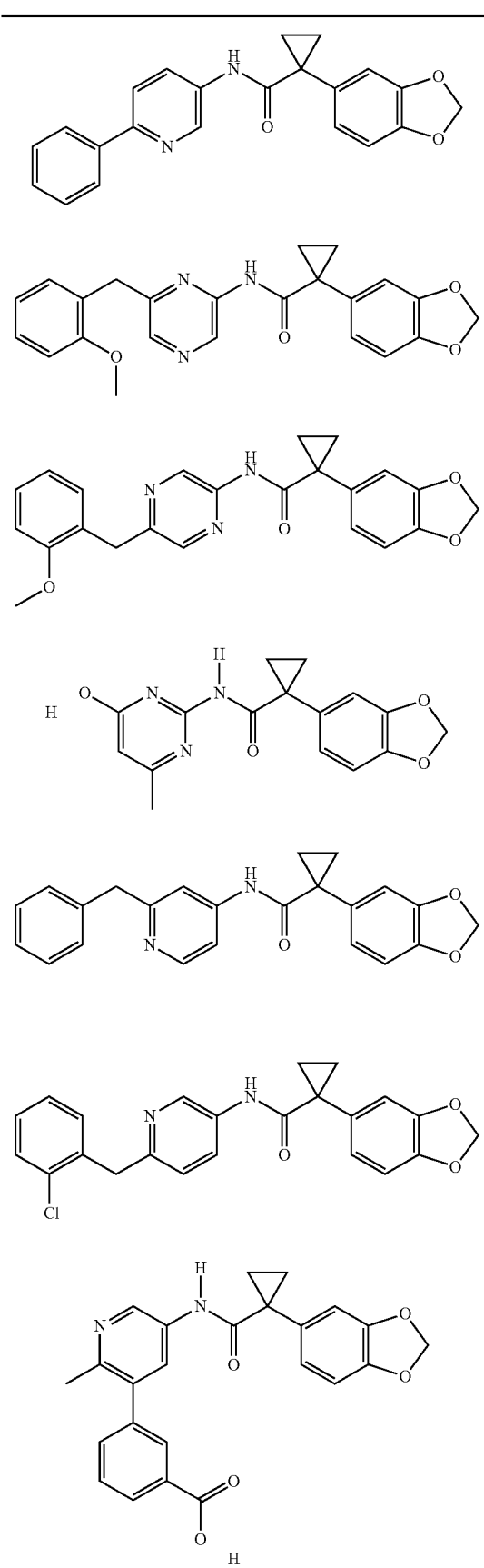
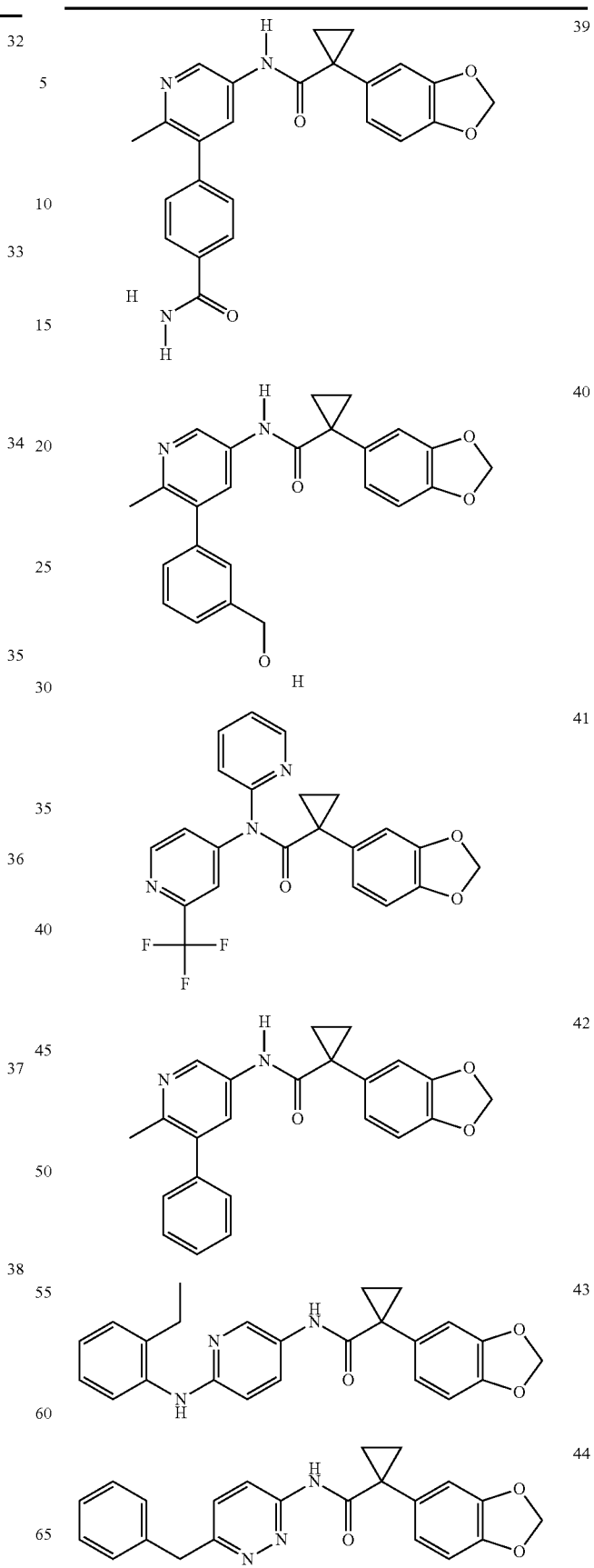

41

TABLE 1-continued

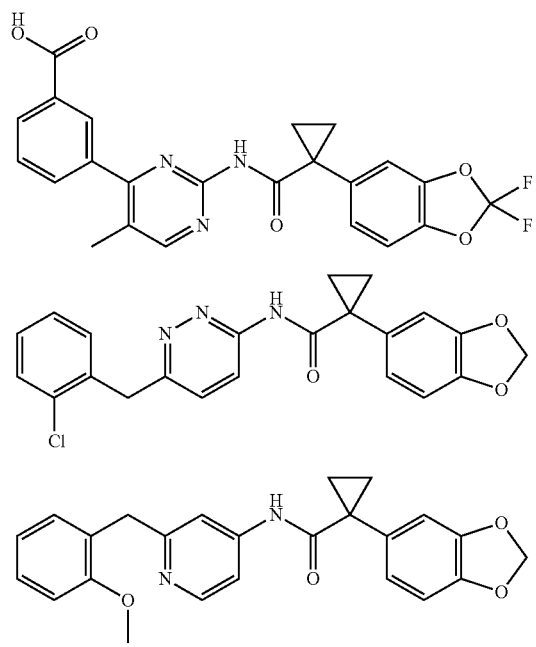

In another embodiment, the present invention relates to a pharmaceutical composition comprising (i) a compound of the present invention; and (ii) a pharmaceutically acceptable carrier. In another embodiment, the pharmaceutical composition further comprises an additional agent selected from the group consisting of a mucolytic agent, bronchodialator, an anti-biotic, an anti-infective agent, an anti-inflammatory agent, CFTR corrector, and a nutritional agent.

In another embodiment, the present invention relates to a method of modulating ABC transporters in a membrane of a cell, comprising the step of contacting said cell with a compound of the present invention. In another embodiment, the ABC transporter is CFTR.

In another embodiment, the present invention relates to a method of treating a condition, disease, or disorder in a patient implicated by ABC transporter activity, comprising the step of administering to said patient a compound of the present invention. In another embodiment, the ABC transporter is CFTR. In another embodiment, said condition, disease, or disorder is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (di), neurophyseal di, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjögren's disease.

In another embodiment, the present invention relates to a kit for use in measuring the activity of a ABC transporter or a fragment thereof in a biological sample in vitro or in vivo, comprising: (i) a first composition comprising a compound of the present invention; and (ii) instructions for: a) contacting the composition with the biological sample; and b) measuring activity of said ABC transporter or a fragment thereof.

General Synthetic Schemes

Compounds of formula I can be prepared by well-known methods in the art. Illustrated below are exemplary methods for the preparation of compounds of formula I. Schemes I below illustrates an exemplary synthetic method for compounds of formula I.

Synthetic Schemes

Compounds of the invention may be prepared by known methods and as illustrated in Schemes I-III.

Scheme I-Preparation of cycloalkyl acids.

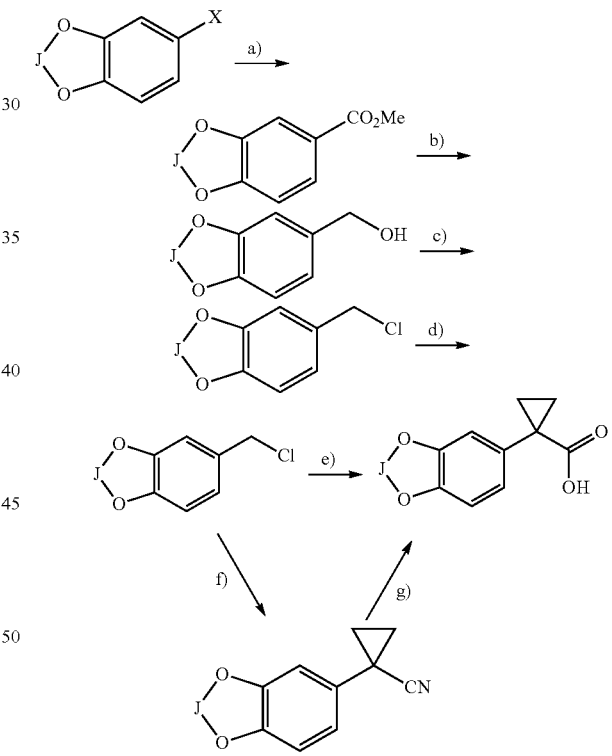

a) X = Br, I; Pd(PPh$_3$)$_4$, CO, MeOH; b) LiAlH$_4$; c) SOCl$_2$; d) NaCN; e) ClCH$_2$CH$_2$Br, NaOH, ΔT; f) ClCH$_2$CH$_2$Br, NaOH; g) NaOH, ΔT.

Scheme II-Amid coupling

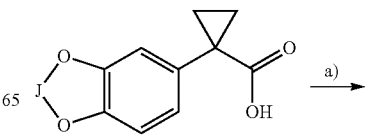

43
-continued

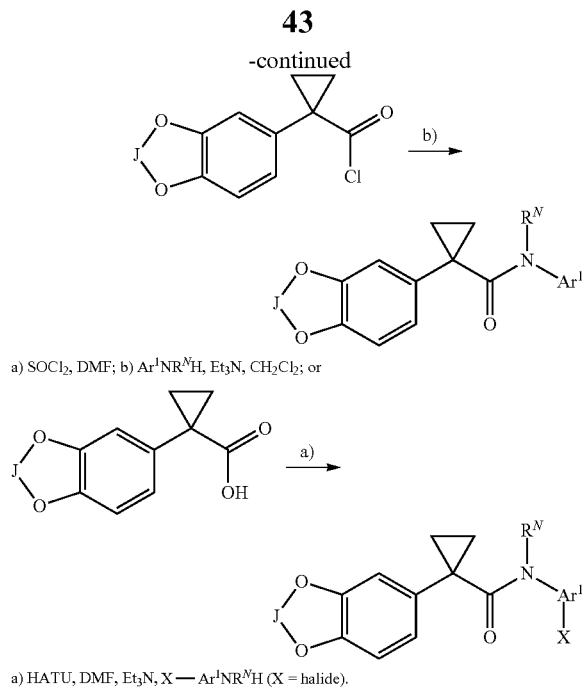

a) SOCl₂, DMF; b) Ar¹NR^N H, Et₃N, CH₂Cl₂; or a) HATU, DMF, Et₃N, X — Ar¹NR^N H (X = halide).

44

One of skill in the art will readily appreciate that synthetic routes suitable for various substituents of the present invention are such that the reaction conditions and steps.

Uses, Formulation and Administration

Pharmaceutically Acceptable Compositions

As discussed above, the present invention provides compounds that are useful as modulators of ABC transporters and thus are useful in the treatment of disease, disorders or conditions such as Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine Scheme III-Derivatization of heteroarylhalides

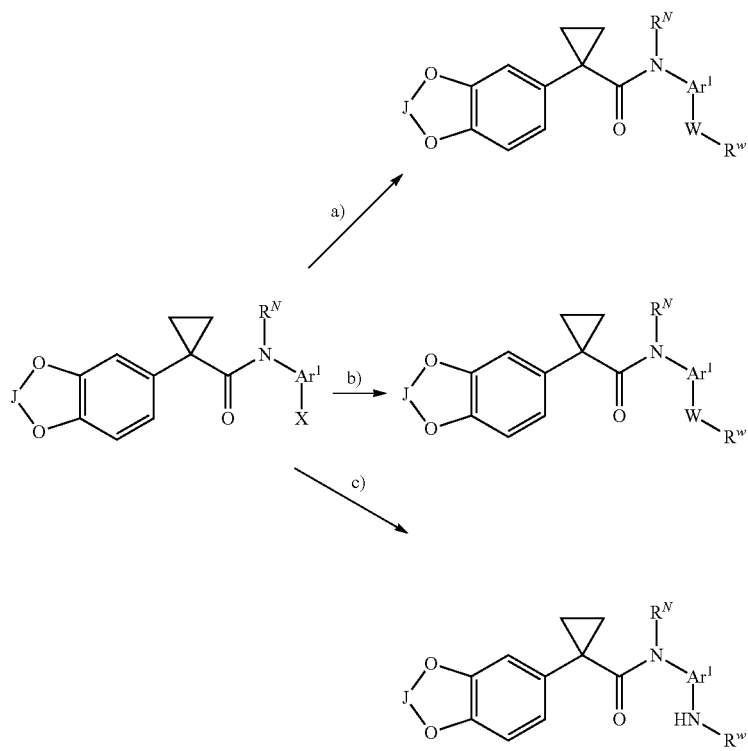

a) R^w—W—(OR')₂ (R' = H, Me), Pd(0), base, DMF, H₂O; b) R^w—CH₂ZnX, (dppf)₂PdCl₂, CH₂Cl₂, THF (X = Cl, Br); c) (dppf)₂PdCl₂, Xantphos, K^tOBu, dioxane, Et₃N, R^w—NH₂.

neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker syndrome, COPD, dry-eye disease, and Sjögren's disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an ATP-Binding Cassette Transporters.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (S Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential (Vm) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Preparation of
1-benzo[1,3]dioxol-5-yl-cyclopronanecarboxylic acid

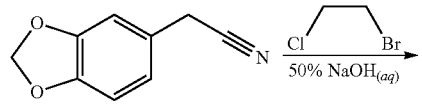

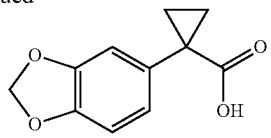

A mixture of 2-(benzo[d][1,3]dioxol-5-yl)acetonitrile (5.10 g 31.7 mmol), 1-bromo-2-chloro-ethane (9.00 mL 109 mmol), and benzyltriethylammonium chloride (0.181 g, 0.795 mmol) was heated at 70° C. and then 50% (wt./wt.) aqueous sodium hydroxide (26 mL) was slowly added to the mixture. The reaction was stirred at 70° C. for 24 hours and then heated at 130° C. for 48 hours. The dark brown reaction mixture was diluted with water (400 mL) and extracted once with an equal volume of ethyl acetate and once with an equal volume of dichloromethane. The basic aqueous solution was acidified with concentrated hydrochloric acid to pH less than one and the precipitate filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 80%) ESI-MS m/z calc. 206.1. Found 207.1 (M+1)$^+$. Retention time 2.37 minutes. $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H).

Preparation of 1-(2,2-difluoro-benzo[1,3]dioxol-5-yl)-cyclopropanecarboxylic acid

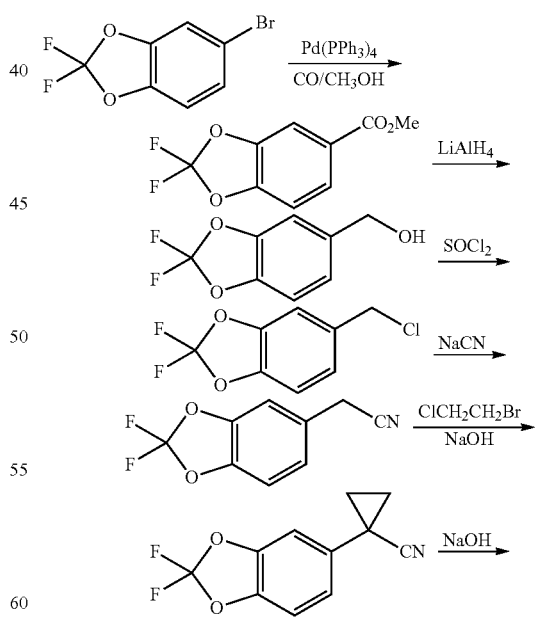

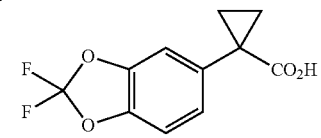

Step a: 2,2-Difluoro-benzo[1,3]dioxole-5-carboxylic acid methyl ester

A solution of 5-bromo-2,2-difluoro-benzo[1,3]dioxole (11.8 g, 50.0 mmol) and tetrakis(triphenylphosphine)palladium (0) [Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give crude 2,2-difluoro-benzo[1,3]dioxole-5-carboxylic acid methyl ester (11.5 g), which was used directly in the next step.

Step b: (2,2-Difluoro-benzo[1,3]dioxol-5-yl)-methanol

Crude 2,2-difluoro-benzo[1,3]dioxole-5-carboxylic acid methyl ester (11.5 g) dissolved in 20 mL of anhydrous tetrahydrofuran (THF) was slowly added to a suspension of lithium aluminum hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 38 mmol, 76% over two steps) as a colorless oil.

Step c: 5-Chloromethyl-2,2-difluoro-benzo[1,3]dioxole

Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the organic layer was dried over sodium sulfate, filtrated, and evaporated to dryness to give crude 5-chloromethyl-2,2-difluoro-benzo[1,3]dioxole (4.4 g) which was used directly in the next step without further purification.

Step d: (2,2-Difluoro-benzo[1,3]dioxol-5-yl)-acetonitrile

A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The organic layer was dried over sodium sulfate and evaporated to dryness to give crude (2,2-difluoro-benzo[1,3]dioxol-5-yl)-acetonitrile (3.3 g) which was used directly in the next step.

Step e: 1-(2,2-Difluoro-benzo[1,3]dioxol-5-yl)-cyclopropanecarbonitrile

Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C. The mixture was stirred overnight at 70° C. before the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

Step f: 1-(2,2-Difluoro-benzo[1,3]dioxol-5-yl)-cyclopropanecarboxylic acid 1-(2,2-Difluoro-benzo[1,3]dioxol-5-yl)-cyclopropanecarbonitrile (crude from the last step) was refluxed in 10% aqueous sodium hydroxide (50 mL) for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 1.6% over four steps). ESI-MS m/z calc. 242.04. Found 241.58 (M+1); $^1$H NMR (CDCl$_3$) δ 7.14-7.04 (m, 2H), 6.98-6.96 (m, 1H), 1.74-1.64 (m, 2H), 1.26-1.08 (m, 2H).

Preparation of 1-(benzo[d][1,3]dioxol-5-yl)-N-(5-bromo-6-methylpyridin-3-yl)cyclopropanecarboxamide

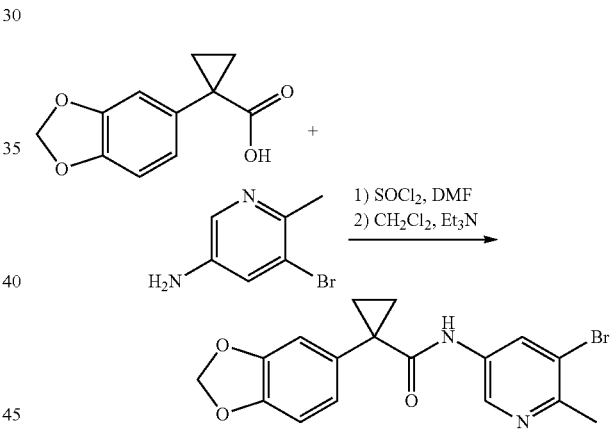

1-Benzo[1,3]dioxol-5-yl-cyclopropanecarboxylic acid (2.76 g, 13.4 mmol) was placed in an oven-dried flask under nitrogen. Thionyl chloride (3.0 mL) and N,N-dimethylformamide (0.3 mL) were added and the solution was allowed to stir for 10 minutes at room temperature. The excess thionyl chloride was removed under vacuum and the resulting solid was suspended in 10 mL of anhydrous dichloromethane. This solution was then slowly added to a solution of 5-bromo-6-methylpyridin-3-amine (2.50 g, 13.4 mmol) in 10 mL of anhydrous dichloromethane containing triethylamine (5.64 mL, 40.2 mmol). The resulting mixture was allowed to stir for 10 minutes at room temperature. The crude product was then washed three times with a saturated aqueous solution of sodium bicarbonate, followed by two washes with a saturated aqueous solution of sodium chloride. The organic layer was dried over sodium sulfate, evaporated to dryness, and the resulting yellow powder (3.62 g, 9.65 mmol, 72.0%) was used without further purification. ESI-MS m/z calc. 374.0. Found; 375.1 (M+1) Retention time 2.30 minutes. $^1$H NMR (400 MHz, CD$_3$CN) δ 8.38 (d, J=2.2 Hz, 1H), 8.14 (d, J=2.2 Hz, 1H), 7.80-7.60 (m, 1H), 7.08-6.95 (s, 2H), 6.89 (dd, J=1.2, 7.3 Hz, 1H), 6.01 (s, 2H), 2.54 (s, 3H), 1.59-1.50 (m, 2H), 1.19-1.09 (m, 2H).

Preparation of 1-(benzo[d][1,3]dioxol-5-yl)-N-(6-methyl-5-phenylpyridin-3-yl)cyclopropanecarboxamide

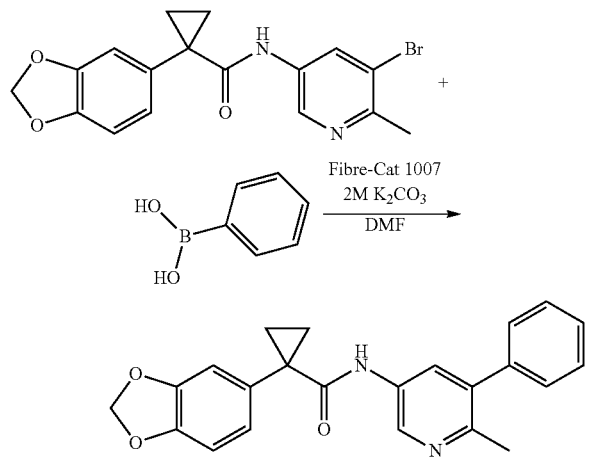

1-(Benzo[d][1,3]dioxol-5-yl)-N-(5-bromo-6-methylpyridin-3-yl)cyclopropanecarboxamide (38 mg, 0.10 mmol) was dissolved in 1 mL of N,N-dimethylformamide (DMF) containing 0.2 mL of a 2M aqueous solution of potassium carbonate and 12 mg of Fibre-Cat 1007. The reaction mixture was then heated to 80° C. for 16 hours. The resulting material was cooled to room temperature, filtered, and purified by reverse-phase preparative liquid chromatography utilizing a gradient of 0-99% acetonitrile in water containing 0.05% trifluoroacetic acid to yield the pure product. ESI-MS m/z calc. 372.2. Found 373.2 (M+1)⁺. Retention time 1.80 minutes.

Preparation of 4-(5-(1-(benzo[d][1,3]dioxol-5-yl)cyclopropanecarboxamido)-2-methylpyridin-3-yl)benzamide

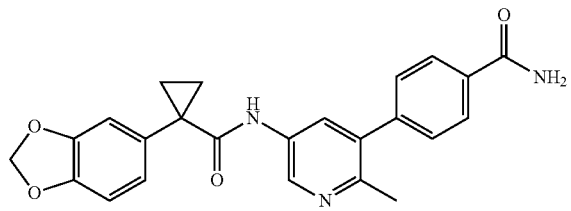 [SMILES: Cc1ncc(NC(=O)C2(c3ccc4c(c3)OCO4)CC2)cc1-c1ccc(C(N)=O)cc1]

4-(5-(1-(Benzo[d][1,3]dioxol-5-yl)cyclopropanecarboxamido)-2-methylpyridin-3-yl)benzamide was prepared from 4-carbamoylphenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 4-(5-(1-(benzo[d][1,3]dioxol-5-yl)cyclopropanecarboxamido)-2-methylpyridin-3-yl)-N-methylbenzamide

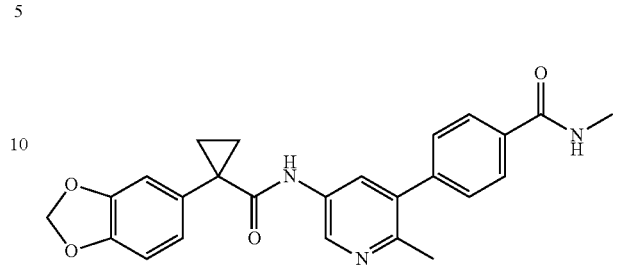

4-(5-(1-(Benzo[d][1,3]dioxol-5-yl)cyclopropanecarboxamido)-2-methylpyridin-3-yl)-N-methylbenzamide was prepared from 4-(methylcarbamoyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide

Preparation of 1-(benzo[d][1,3]dioxol-5-yl)-N-(5-(3-(hydroxymethyl)phenyl)-6-methylpyridin-3-yl)cyclopropanecarboxamide

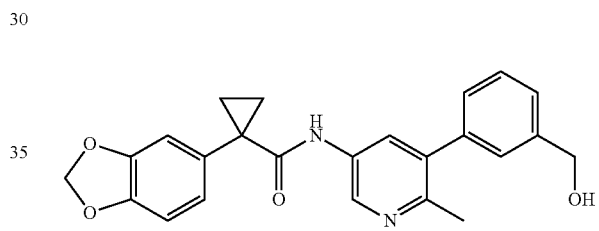

1-(Benzo[d][1,3]dioxol-5-yl)-N-(5-(3-(hydroxymethyl)phenyl)-6-methylpyridin-3-yl)cyclopropanecarboxamide was prepared from 3-(hydroxymethyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(benzo[d][1,3]dioxol-5-yl)-N-(6-methyl-5-(4-(N-methylsulfamoyl)phenyl)pyridin-3-yl)cyclopropanecarboxamide

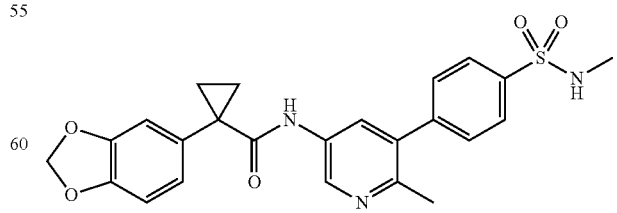

1-(Benzo[d][1,3]dioxol-5-yl)-N-(6-methyl-5-(4-(N-methylsulfamoyl)phenyl)pyridin-3-yl)cyclopropanecarboxamide was prepared from 4-(N-methylsulfamoyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(benzo[d][1,3]dioxol-5-yl)-N-(5-(3-(N,N-dimethylsulfamoyl)phenyl)-6-methylpyridin-3-yl)cyclopropanecarboxamide

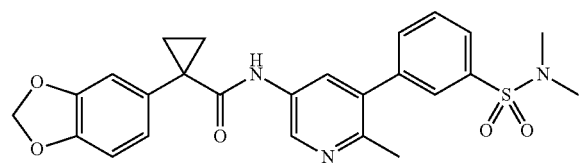 [SMILES: Cc1ncc(NC(=O)C2(c3ccc4c(c3)OCO4)CC2)cc1-c1cccc(S(=O)(=O)N(C)C)c1]

1-(Benzo[d][1,3]dioxol-5-yl)-N-(5-(3-(N,N-dimethylsulfamoyl)phenyl)-6-methylpyridin-3-yl)cyclopropanecarboxamide was prepared from 3-(N,N-dimethylsulfamoyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(benzo[d][1,3]dioxol-5-yl)-N-(5-(4-(N,N-dimethylsulfamoyl)phenyl)-6-methylpyridin-3-yl)cyclopropanecarboxamide

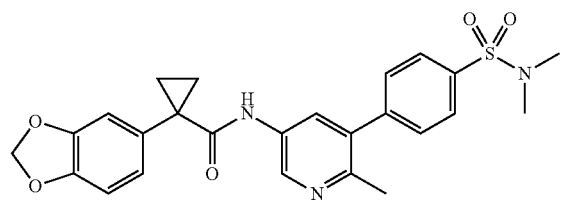 [SMILES: Cc1ncc(NC(=O)C2(c3ccc4c(c3)OCO4)CC2)cc1-c1ccc(S(=O)(=O)N(C)C)cc1]

1-(Benzo[d][1,3]dioxol-5-yl)-N-(5-(4-(N,N-dimethylsulfamoyl)phenyl)-6-methylpyridin-3-yl)cyclopropanecarboxamide was prepared from 4-(N,N-dimethylsulfamoyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 3-(5-(1-(benzo[d][1,3]dioxol-5-yl)cyclopropanecarboxamido)-2-methylpyridin-3-yl)benzamide

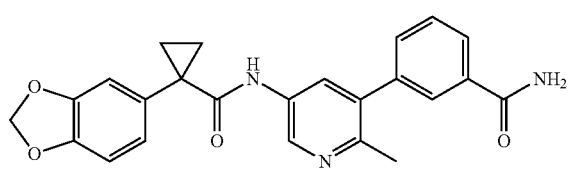 [SMILES: Cc1ncc(NC(=O)C2(c3ccc4c(c3)OCO4)CC2)cc1-c1cccc(C(N)=O)c1]

3-(5-(1-(Benzo[d][1,3]dioxol-5-yl)cyclopropanecarboxamido)-2-methylpyridin-3-yl)benzamide was prepared from 3-carbamoylphenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 3-(5-(1-(benzo[d][1,3]dioxol-5-yl)cyclopropanecarboxamido)-2-methylpyridin-3-yl)benzoic acid

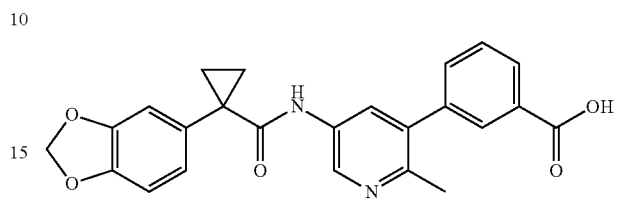

3-(5-(1-(Benzo[d][1,3]dioxol-5-yl)cyclopropanecarboxamido)-2-methylpyridin-3-yl)benzoic acid was prepared from 3-boronobenzoic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(benzo[d][1,3]dioxol-5-yl)-N-(5-(4-(hydroxymethyl)phenyl)-6-methylpyridin-3-yl)cyclopropanecarboxamide

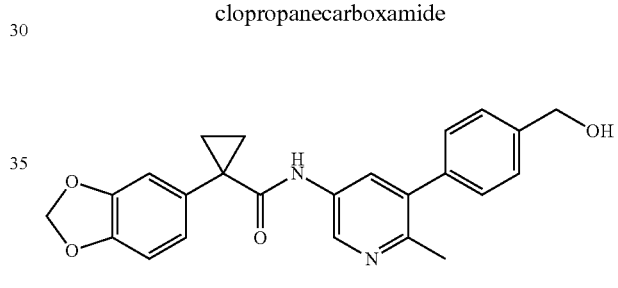

1-(Benzo[d][1,3]dioxol-5-yl)-N-(5-(4-(hydroxymethyl)phenyl)-6-methylpyridin-3-yl)cyclopropanecarboxamide was prepared from 4-(hydroxymethyl)phenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(benzo[d][1,3]dioxol-5-yl)-N-(6-methyl-5-(3-sulfamoylphenyl)pyridin-3-yl)cyclopropanecarboxamide

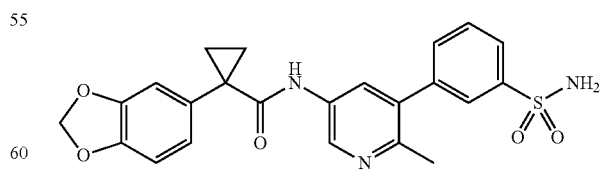

1-(Benzo[d][1,3]dioxol-5-yl)-N-(6-methyl-5-(3-sulfamoylphenyl)pyridin-3-yl)cyclopropanecarboxamide was prepared from 3-sulfamoylphenylboronic acid and 1-(benzo[d][1,3]dioxol-5-yl)-N-(5-bromo-6-methylpyridin-3-yl)cyclopropanecarboxamide in a manner analogous to that of 1-(benzo[d][1,3]dioxol-5-yl)-N-(6-methyl-5-phenylpyridin-3-yl)cyclopropanecarboxamide.

Preparation of 1-(Benzo[d][1,3]dioxol-5-yl)-N-(6-isopropylpyridin-3-yl)cyclopropanecarboxamide

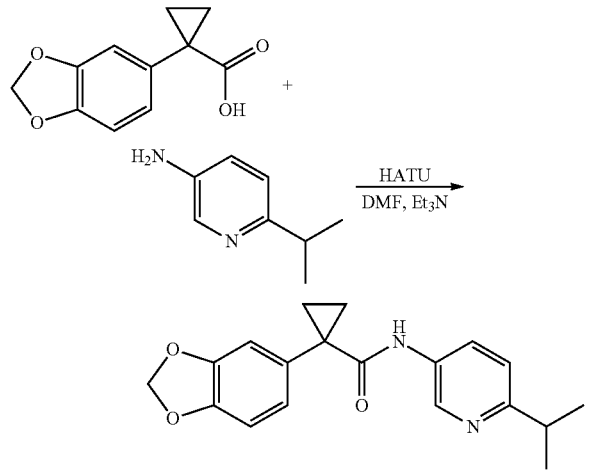

1-(Benzo[d][1,3]dioxol-5-yl)cyclopropanecarboxylic acid (20.6 mg, 0.100 mmol) and 6-isopropylpyridin-3-amine (13.6 g, 0.100 mmol) were dissolved in N,N-dimethylformamide (DMF, 1 mL) containing triethylamine (0.042 mL, 0.300 mmol). O-(7-Azabenzotriazol-1-yl)-N,N,N',N'-tetramethyluronium hexafluorophosphate (HATU, 39.9 mg, 0.105 mmol) was added and the solution was allowed to stir for 3 hours. The mixture was then purified by reverse phase preparative liquid chromatography utilizing a gradient of 0-99% acetonitrile in water containing 0.05% trifluoroacetic acid to yield the pure product. ESI-MS m/z calc. 324.2. Found 325.3 (M+1)⁺. Retention time 2.14 minutes.

Preparation of 1-(benzo[d][1,3]dioxol-5-yl)-N-(6-(2-methoxybenzyl)pyridin-3-yl)cyclopropanecarboxamide

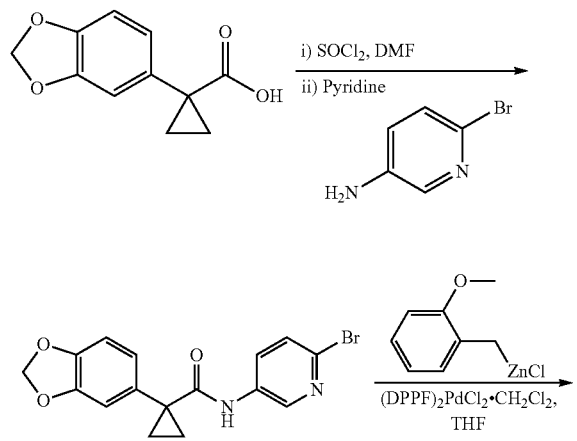

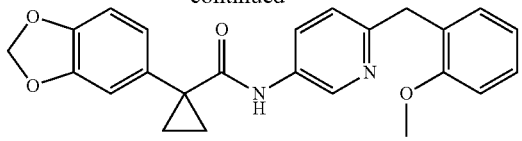

Step a: 1-(Benzo[d][1,3]dioxol-5-yl)-N-(6-bromopyridin-3-yl)cyclopropanecarboxamide To 1-(benzo[d][1,3]dioxol-5-yl)cyclopropanecarboxylic acid (9.50 g, 46.00 mmol), thionyl chloride (10.00 mL, 138.00 mmol) and DMF (4 drops) were added and the mixture was stirred and heated at 60° C. for thirty minutes. The excess thionyl chloride was evaporated under reduced pressure. A portion of the acid chloride (23.20 mmol) was dissolved in pyridine (15 mL) and was slowly added to 6-bromopyridin-3-amine (23.20 mmol) in pyridine (10 mL). The reaction mixture was stirred at 110° C. for one hour and thirty minutes. The pyridine was evaporated under reduced pressure. The resulting mixture was dissolved in dichloromethane (200 mL) and washed with 1 N NaOH (4×50 mL). The organic layer was dried over anhydrous Na₂SO₄ and evaporated under reduced pressure. The crude product was purified by column chromatography on silica gel to yield 1-(benzo[d][1,3]dioxol-5-yl)-N-(6-bromopyridin-3-yl)cyclopropanecarboxamide (4 g, 48%).

Step b: 1-(Benzo[d][1,3]dioxol-5-yl)-N-(6-(2-methoxybenzyl)pyridin-3-yl)cyclopropanecarboxamide A solution of (2-methoxybenzyl)zinc(II) chloride (4.44 mL, 0.5 M, 2.20 mmol) in THF and (DPPF)₂PdCl₂·CH₂Cl₂ (45 mg, 0.056 mmol) was stirred at room temperature for 20 minutes. To this, a slurry of 1-(benzo[d][1,3]dioxol-5-yl)-N-(6-bromopyridin-3-yl)cyclopropanecarboxamide (200 mg, 0.56 mmol) in THF (4 mL) was added and the reaction mixture was heated to 150° C. in a microwave reactor for 10 minutes. The resulting material was cooled to room temperature. Na₂EDTA and saturated aqueous NH₄Cl were added to the reaction and the mixture was stirred at room temperature for 30 minutes. The product was extracted using dichloromethane. The organic layer was dried over anhydrous Na₂SO₄ and evaporated under reduced pressure. The crude product was purified by column chromatography on silica gel to yield 1-(benzo[d][1,3]dioxol-5-yl)-N-(6-(2-methoxybenzyl)pyridin-3-yl)cyclopropanecarboxamide (152 mg, 68%).

Preparation of 1-(benzo[d][1,3]dioxol-5-yl)-N-(6-(2-chlorobenzyl)pyridin-3-yl)cyclopropanecarboxamide

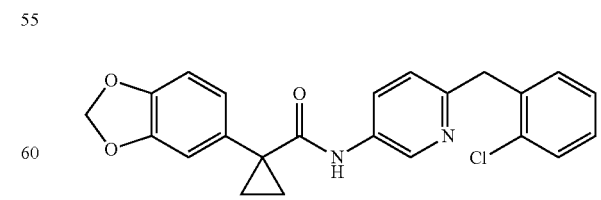

1-(Benzo[d][1,3]dioxol-5-yl)-N-(6-(2-chlorobenzyl)pyridin-3-yl)cyclopropanecarboxamide was synthesized using the procedure of 1-(benzo[d][1,3]dioxol-5-yl)-N-(6-(2-methoxybenzyl)pyridin-3-yl)cyclopropanecarboxamide from (2-chlorobenzyl)zinc(II) chloride and 1-(benzo[d][1,3]dioxol-5-yl)-N-(6-bromopyridin-3-yl)cyclopropanecarboxamide.

Preparation of 1-(benzo[d][1,3]dioxol-5-yl)-N-(6-benzylpyridin-3-yl)cyclopropanecarboxamide

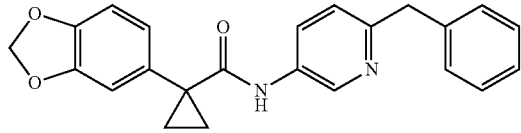 [SMILES: O=C(Nc1ccc(Cc2ccccc2)nc1)C1(c2ccc3c(c2)OCO3)CC1]

1-(Benzo[d][1,3]dioxol-5-yl)-N-(6-benzylpyridin-3-yl)cyclopropanecarboxamide was synthesized using the procedure of 1-(benzo[d][1,3]dioxol-5-yl)-N-(6-(2-methoxybenzyl)pyridin-3-yl)cyclopropanecarboxamide using benzylzinc(II) bromide and 1-(benzo[d][1,3]dioxol-5-yl)-N-(6-bromopyridin-3-yl)cyclopropanecarboxamide.

Preparation of 1-(benzo[d][1,3]dioxol-5-yl)-N-(6-phenylpyridin-3-yl)cyclopropanecarboxamide

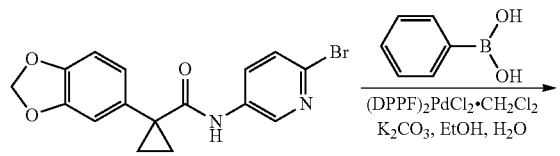

To 1-(benzo[d][1,3]dioxol-5-yl)-N-(6-bromopyridin-3-yl)cyclopropanecarboxamide (72 mg, 0.20 mmol), phenylboronic acid (16 mg, 0.13 mmol), K₂CO₃ (19 mg, 0.14 mmol) and (DPPF)₂PdCl₂.CH₂Cl₂ (6 mg, 0.007 mmol), ethanol (545 uL) and water (55 uL) were added. The reaction mixture was heated to 150° C. in a microwave reactor for 10 minutes. The resulting material was cooled to room temperature. The reaction mixture was diluted with dichloromethane, filtered, and the filtrate was concentrated. The crude product was dissolved in DMSO (1 mL), filtered, and purified by reverse phase preparative HPLC to yield 1-(benzo[d][1,3]dioxol-5-yl)-N-(6-phenylpyridin-3-yl)cyclopropanecarboxamide as a TFA salt (8.5 mg, 0.018 mmol, 13%).

Preparation of 1-(benzo[d][1,3]dioxol-5-yl)-N-(6-(2-methoxyphenyl)pyridin-3-yl)cyclopropanecarboxamide

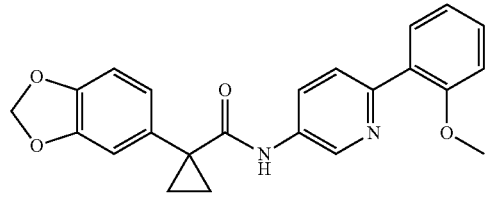 [SMILES: COc1ccccc1-c1ccc(NC(=O)C2(c3ccc4c(c3)OCO4)CC2)cn1]

1-(Benzo[d][1,3]dioxol-5-yl)-N-(6-(2-methoxyphenyl)pyridin-3-yl)cyclopropanecarboxamide was synthesized using the procedure of 1-(benzo[d][1,3]dioxol-5-yl)-N-(6-phenylpyridin-3-yl)cyclopropanecarboxamide from 2-methoxyphenylboronic acid and 1-(benzo[d][1,3]dioxol-5-yl)-N-(6-bromopyridin-3-yl)cyclopropanecarboxamide.

Preparation of 1-(benzo[d][1,3]dioxol-5-yl)-N-(6-(2-chlorophenyl)pyridin-3-yl)cyclopropanecarboxamide

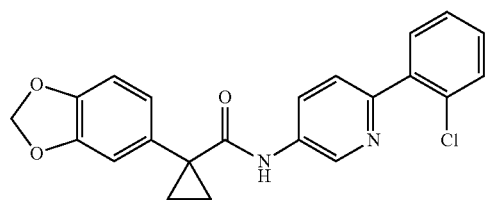 [SMILES: O=C(Nc1ccc(-c2ccccc2Cl)nc1)C1(c2ccc3c(c2)OCO3)CC1]

1-(Benzo[d][1,3]dioxol-5-yl)-N-(6-(2-chlorophenyl)pyridin-3-yl)cyclopropanecarboxamide was synthesized using the procedure of 1-(benzo[d][1,3]dioxol-5-yl)-N-(6-phenylpyridin-3-yl)cyclopropanecarboxamide from 2-chlorophenylboronic acid and 1-(benzo[d][1,3]dioxol-5-yl)-N-(6-bromopyridin-3-yl)cyclopropanecarboxamide.

Preparation of 1-(benzo[d][1,3]dioxol-5-yl)-N-(6-(2-methoxyphenylamino)pyridin-3-yl)cyclopropanecarboxamide

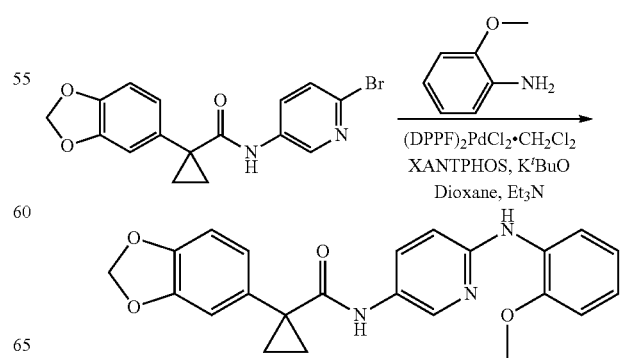

To 1-(benzo[d][1,3]dioxol-5-yl)-N-(6-bromopyridin-3-yl)cyclopropanecarboxamide (72 mg, 0.2 mmol) in dioxane (0.400 mL), XANTPHOS (2.3 mg, 0.004 mmol), K$^t$BuO (31 mg, 0.28 mmol), (DPPF)$_2$PdCl$_2$·CH$_2$Cl$_2$ (3.00 mg, 0.004 mmol), and 2-methoxyaniline (30 mg, 0.24 mmol), and Et$_3$N (0.200 mL) were added. The reaction mixture was heated to 150° C. in a microwave reactor for 10 minutes. The resulting material was cooled to room temperature. The crude product was purified by column chromatography on silica gel to yield 1-(benzo[d][1,3]dioxol-5-yl)-N-(6-(2-methoxyphenylamino)pyridin-3-yl)cyclopropanecarboxamide which was then treated with HCl in MeOH to form the HCl salt (2.3 mg, 0.0053 mmol, 2.7%). ESI-MS m/z calc. 403.2. Found; 404.5 (M+1)$^+$ Retention time 2.29 minutes.

Preparation of 1-(benzo[d][1,3]dioxol-5-yl)-N-(6-benzylpyrazin-2-yl)cyclopropanecarboxamide

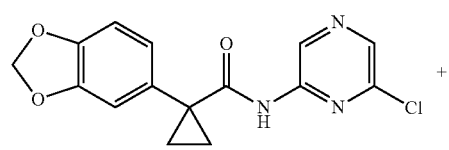

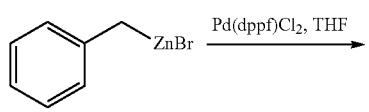

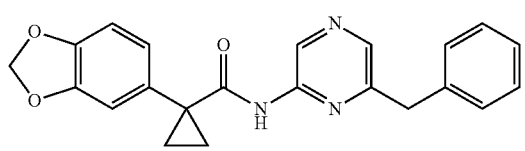

To a 0.5 M solution of benzylzinc(II) bromide in THF (0.8 mL, 0.4 mmol) was added [1,1'-bis(diphenylphosphino)ferrocene]dichloropalladium(II) (8 mg, 0.01 mmol) and the reaction was stirred under nitrogen for 20 minutes. 1-(Benzo[d][1,3]dioxol-5-yl)-N-(6-chloropyrazin-2-yl)cyclopropanecarboxamide (32 mg, 0.1 mmol) was added and the reaction was irradiated in a microwave reactor for 10 minutes at 150° C. The reaction was quenched with a saturated ammonium chloride solution (2 mL) and a saturated ethylenediamine tetraacetic acid disodium salt solution (2 mL). The mixture was stirred for 30 minutes before it was extracted with dichloromethane (3×4 mL). The organics were dried over Na$_2$SO$_4$ and evaporated. The crude product was dissolved in DMSO (1 mL) and purified by reverse-phase preparative liquid chromatography utilizing a gradient of 0-99% acetonitrile in water containing 0.05% trifluoracetic acid to yield the pure product (2.0 mg, 0.0054 mmol, 5.4%). ESI-MS m/z calc. 373.14. Found 374.1 (M+1)+; retention time 3.32 minutes.

Preparation of 1-(benzo[d][1,3]dioxol-5-yl)-N-(6-(2-methoxybenzyl)pyrazin-2-yl)cyclopropanecarboxamide

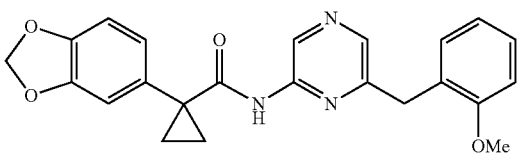 [SMILES: COc1ccccc1Cc1cncc(NC(=O)C2(c3ccc4c(c3)OCO4)CC2)n1]

The title compound was made in a similar procedure as reported for 1-(benzo[d][1,3]dioxol-5-yl)-N-(6-benzylpyrazin-2-yl)cyclopropanecarboxamide from (2-methoxybenzyl)zinc(II) chloride and 1-(benzo[d][1,3]dioxol-5-yl)-N-(6-chloropyrazin-2-yl)cyclopropanecarboxamide.

Preparation of 1-(benzo[d][1,3]dioxol-5-yl)-N-(6-(2-chlorobenzyl)pyrazin-2-yl)cyclopropanecarboxamide

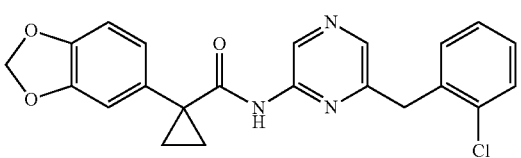 [SMILES: O=C(Nc1cncc(Cc2ccccc2Cl)n1)C1(c2ccc3c(c2)OCO3)CC1]

The title compound was made using a similar procedure as reported for 1-(benzo[d][1,3]dioxol-5-yl)-N-(6-benzylpyrazin-2-yl)cyclopropanecarboxamide from (2-chlorobenzyl)zinc(II) chloride and 1-(benzo[d][1,3]dioxol-5-yl)-N-(6-chloropyrazin-2-yl)cyclopropanecarboxamide.

Preparation of 1-(benzo[d][1,3]dioxol-5-yl)-N-(5-(2-chlorobenzyl)pyrazin-2-yl)cyclopropanecarboxamide

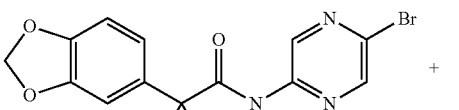

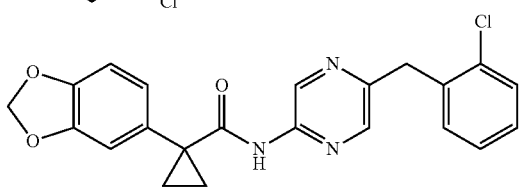

To a 0.5 M solution of (2-chlorobenzyl)zinc(II) chloride in THF (0.8 mL, 0.4 mmol) was added [1,1'-bis(diphenylphosphino)ferrocene]dichloropalladium(II) (8 mg, 0.01 mmol)

and the reaction was stirred under nitrogen for 20 minutes. 1-(Benzo[d][1,3]dioxol-5-yl)-N-(5-bromopyrazin-2-yl)cyclopropanecarboxamide (36 mg, 0.10 mmol) was added and the reaction was irradiated in the microwave for 10 minutes at 150° C. The reaction was quenched with a saturated ammonium chloride solution (2 mL) and a saturated ethylenediamine tetraacetic acid disodium salt solution (2 mL). The mixture was stirred for 30 minutes before it was extracted with dichloromethane (3×4 mL). The organics were dried over Na$_2$SO$_4$ and evaporated. The crude product was dissolved in DMSO (1 mL) and purified by reverse-phase preparative liquid chromatography utilizing a gradient of 0-99% acetonitrile in water containing 0.05% trifluoracetic acid to yield the pure product (16 mg, 0.039 mmol, 39%). ESI-MS m/z calc. 407.1. Found 408.2 (M+1)+; retention time 3.82 minutes.

Preparation of 1-(benzo[d][1,3]dioxol-5-yl)-N-(5-(2-methoxybenzyl)pyrazin-2-yl)cyclopropanecarboxamide

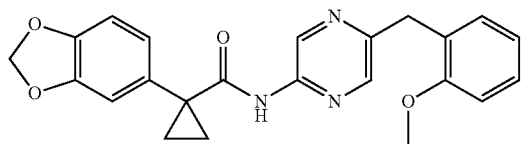 [SMILES: COc1ccccc1Cc1cnc(NC(=O)C2(c3ccc4c(c3)OCO4)CC2)cn1]

The title compound was made using a similar procedure as described for 1-(benzo[d][1,3]dioxol-5-yl)-N-(5-(2-chlorobenzyl)pyrazin-2-yl)cyclopropanecarboxamide from (2-methoxybenzyl)zinc(II) chloride and 1-(benzo[d][1,3]dioxol-5-yl)-N-(5-bromopyrazin-2-yl)cyclopropanecarboxamide.

Preparation of 1-(benzo[d][1,3]dioxol-5-yl)-N-(5-benzylpyrazin-2-yl)cyclopropanecarboxamide

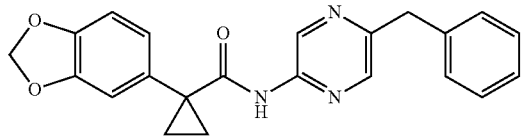 [SMILES: O=C(Nc1cnc(Cc2ccccc2)cn1)C1(c2ccc3c(c2)OCO3)CC1]

The title compound was made using a similar procedure as reported for 1-(benzo[d][1,3]dioxol-5-yl)-N-(5-(2-chlorobenzyl)pyrazin-2-yl)cyclopropanecarboxamide from benzylzinc(II) bromide and 1-(benzo[d][1,3]dioxol-5-yl)-N-(5-bromopyrazin-2-yl)cyclopropanecarboxamide.

Preparation of 1-(benzo[d][1,3]dioxol-5-yl)-N-(5-(2-methoxyphenylamino)pyrazin-2-yl)cyclopropanecarboxamide

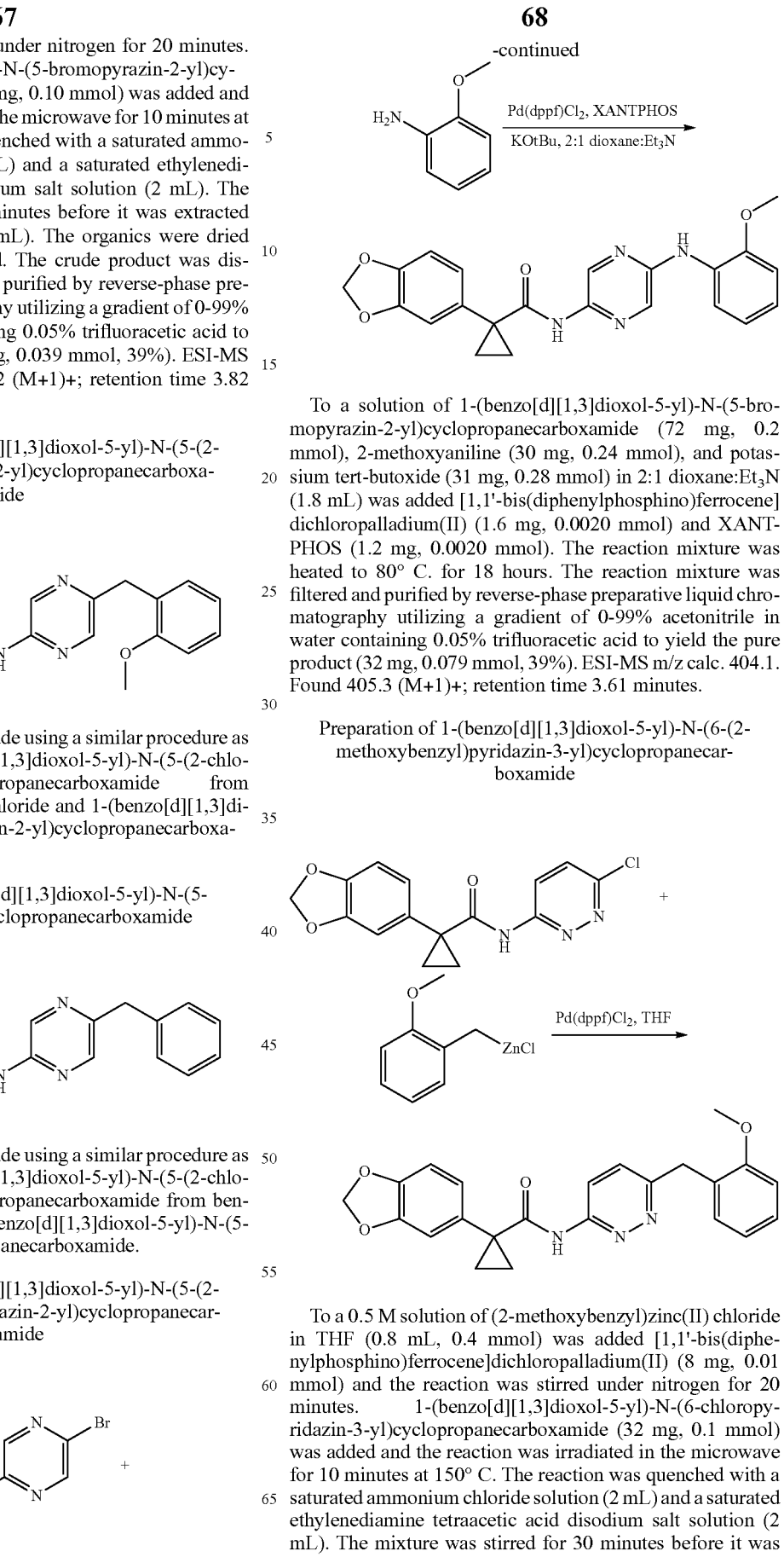

To a solution of 1-(benzo[d][1,3]dioxol-5-yl)-N-(5-bromopyrazin-2-yl)cyclopropanecarboxamide (72 mg, 0.2 mmol), 2-methoxyaniline (30 mg, 0.24 mmol), and potassium tert-butoxide (31 mg, 0.28 mmol) in 2:1 dioxane:Et$_3$N (1.8 mL) was added [1,1'-bis(diphenylphosphino)ferrocene]dichloropalladium(II) (1.6 mg, 0.0020 mmol) and XANTPHOS (1.2 mg, 0.0020 mmol). The reaction mixture was heated to 80° C. for 18 hours. The reaction mixture was filtered and purified by reverse-phase preparative liquid chromatography utilizing a gradient of 0-99% acetonitrile in water containing 0.05% trifluoracetic acid to yield the pure product (32 mg, 0.079 mmol, 39%). ESI-MS m/z calc. 404.1. Found 405.3 (M+1)+; retention time 3.61 minutes.

Preparation of 1-(benzo[d][1,3]dioxol-5-yl)-N-(6-(2-methoxybenzyl)pyridazin-3-yl)cyclopropanecarboxamide To a 0.5 M solution of (2-methoxybenzyl)zinc(II) chloride in THF (0.8 mL, 0.4 mmol) was added [1,1'-bis(diphenylphosphino)ferrocene]dichloropalladium(II) (8 mg, 0.01 mmol) and the reaction was stirred under nitrogen for 20 minutes. 1-(benzo[d][1,3]dioxol-5-yl)-N-(6-chloropyridazin-3-yl)cyclopropanecarboxamide (32 mg, 0.1 mmol) was added and the reaction was irradiated in the microwave for 10 minutes at 150° C. The reaction was quenched with a saturated ammonium chloride solution (2 mL) and a saturated ethylenediamine tetraacetic acid disodium salt solution (2 mL). The mixture was stirred for 30 minutes before it was extracted with dichloromethane (3×4 mL). The organics were dried over Na$_2$SO$_4$ and evaporated. The crude product was dissolved in DMSO (1 mL) and purified by reverse-phase preparative liquid chromatography utilizing a gradient of 0-99% acetonitrile in water containing 0.05% trifluoracetic acid to yield the pure product (21 mg, 0.052 mmol, 52%). ESI-MS m/z calc. 379.2. Found 380.3 (M+1)+; retention time 3.54 minutes.

Preparation of 1-(benzo[d][1,3]dioxol-5-yl)-N-(6-(2-chlorobenzyl)pyridazin-3-yl)cyclopropanecarboxamide

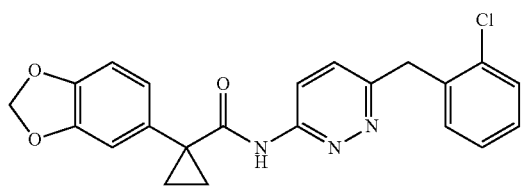 [SMILES: O=C(Nc1ccc(Cc2ccccc2Cl)nn1)C1(c2ccc3c(c2)OCO3)CC1]

The title compound was made using a similar procedure as reported for 1-(benzo[d][1,3]dioxol-5-yl)-N-(6-(2-methoxybenzyl)pyridazin-3-yl)cyclopropanecarboxamide from (2-chlorobenzyl)zinc(II) chloride and 1-(benzo[d][1,3]dioxol-5-yl)-N-(6-chloropyridazin-3-yl)cyclopropanecarboxamide.

Preparation of 4-(benzo[d][1,3]dioxol-5-yl)-N-(6-(cyclohexylmethyl)pyridazin-3-yl)cyclopropanecarboxamide

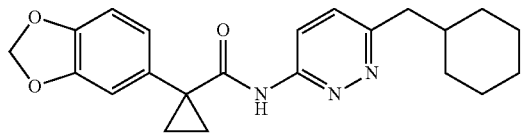 [SMILES: O=C(Nc1ccc(CC2CCCCC2)nn1)C1(c2ccc3c(c2)OCO3)CC1]

The title compound was made in a similar procedure as reported for 1-(benzo[d][1,3]dioxol-5-yl)-N-(6-(2-methoxybenzyl)pyridazin-3-yl)cyclopropane-carboxamide from (cyclohexylmethyl)zinc(II) bromide and 1-(benzo[d][1,3]dioxol-5-yl)-N-(6-chloropyridazin-3-yl) cyclopropanecarboxamide.

Preparation of 1-(benzo[d][1,3]dioxol-5-yl)-N-(6-benzylpyridazin-3-yl)cyclopropanecarboxamide

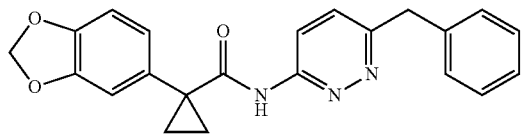 [SMILES: O=C(Nc1ccc(Cc2ccccc2)nn1)C1(c2ccc3c(c2)OCO3)CC1]

The title compound was made using a similar procedure as reported for 1-(benzo[d][1,3]dioxol-5-yl)-N-(6-(2-methoxybenzyl)pyridazin-3-yl)cyclopropanecarboxamide from benzylzinc(II) bromide and 1-(benzo[d][1,3]dioxol-5-yl)-N-(6-chloropyridazin-3-yl)cyclopropanecarboxamide.

Preparation of 1-(benzo[d][1,3]dioxol-5-yl)-N-(2-benzylpyridin-4-yl)cyclopropanecarboxamide

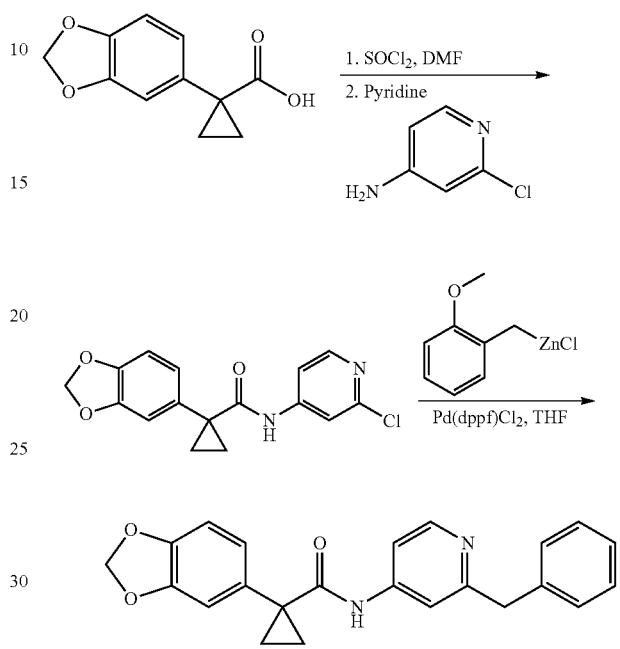

Step a: 1-(Benzo[d][1,3]dioxol-5-yl)-N-(2-chloropyridin-4-yl)cyclopropane-carboxamide To 1-(benzo[d][1,3]dioxol-5-yl)cyclopropanecarboxylic acid (1.5 g, 7.3 mmol) in thionyl chloride (1.6 mL, 21.8 mmol) was added N,N-dimethyl formamide (100 µL). The reaction mixture was stirred at room temperature for 30 minutes before it was evaporated to dryness to yield the desired acid chloride. The acid chloride was added to a solution of 2-chloropyridin-4-amine (0.94 g, 7.3 mmol) in pyridine (10 mL). The reaction was heated to 100° C. for 12 hrs. The reaction was diluted with dichloromethane (30 mL) and washed with 1 N NaOH (3×20 mL). The organics were dried over Na$_2$SO$_4$ and evaporated to dryness. The crude material was purified by silica gel chromatography (eluting with 0-50% ethyl acetate in hexanes) to yield the desired product. ESI-MS m/z calc. 316.06. Found 317.1 (M+1)$^+$. Retention time 2.97 minutes.

Step b: 1-(Benzo[d][1,3]dioxol-5-yl)-N-(2-benzylpyridin-4-yl)cyclopropane-carboxamide To a 0.5 M solution of benzylzinc(II) bromide in THF (0.8 mL, 0.4 mmol) was added [1,1'-bis(diphenylphosphino)ferrocene]dichloropalladium(II) (8 mg, 0.01 mmol) and the reaction was stirred under nitrogen for 20 minutes. 1-(Benzo[d][1,3]dioxol-5-yl)-N-(2-chloropyridin-4-yl)cyclopropanecarboxamide (32 mg, 0.10 mmol) was added and the reaction was irradiated in the microwave for 10 minutes at 150° C. The reaction was quenched with a saturated ammonium chloride solution (2 mL) and a saturated ethylenediamine tetraacetic acid disodium salt solution (2 mL). The mixture was stirred for 30 minutes before it was extracted with dichloromethane (3×4 mL). The organics were dried over Na₂SO₄ and evaporated. The crude product was dissolved in DMSO (1 mL) and purified by reverse-phase preparative liquid chromatography utilizing a gradient of 0-99% acetonitrile in water containing 0.05% trifluoracetic acid to yield the pure product (18 mg, 0.048 mmol, 48%). ESI-MS m/z calc. 372.1. Found 373.3 (M+1)+; retention time 2.44 minutes.

Preparation of 1-(benzo[d][1,3]dioxol-5-yl)-N-(2-(2-methoxybenzyl)pyridin-4-yl)cyclopropanecarboxamide

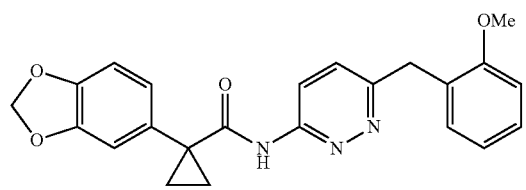 [SMILES: COc1ccccc1Cc1ccc(NC(=O)C2(c3ccc4c(c3)OCO4)CC2)nn1]

The title compound was made using a similar procedure as reported for 1-(benzo[d][1,3]dioxol-5-yl)-N-(2-benzylpyridin-4-yl)cyclopropanecarboxamide from (2-methoxybenzyl) zinc(II) chloride and 1-(Benzo[d][1,3]dioxol-5-yl)-N-(2-chloropyridin-4-yl)cyclopropane-carboxamide.

Preparation of 1-(benzo[d][1,3]dioxol-5-yl)-N-(4-hydroxy-6-methylpyrimidin-2-yl)cyclopropanecarboxamide

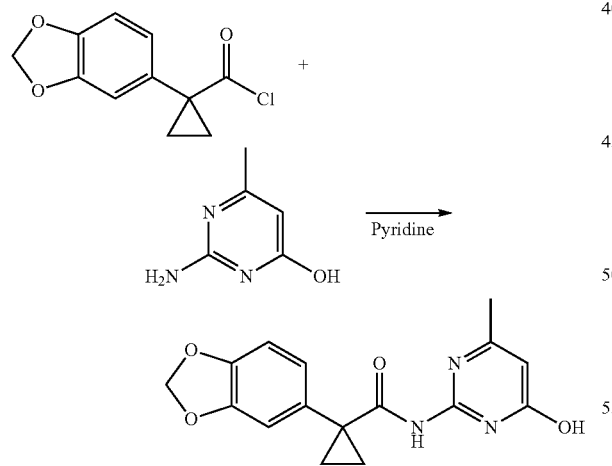

To 1-(benzo[d][1,3]dioxol-5-yl)cyclopropanecarbonyl chloride (45 mg, 0.2 mmol) in pyridine (2 mL) was added 2-amino-6-methylpyrimidin-4-ol (25 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 313.1. Found 314.1 (M+1)⁺. Retention time 2.31 minutes.

Preparation of 1-(benzo[d][1,3]dioxol-5-yl)-N-(4-methylpyrimidin-2-yl)cyclopropanecarboxamide

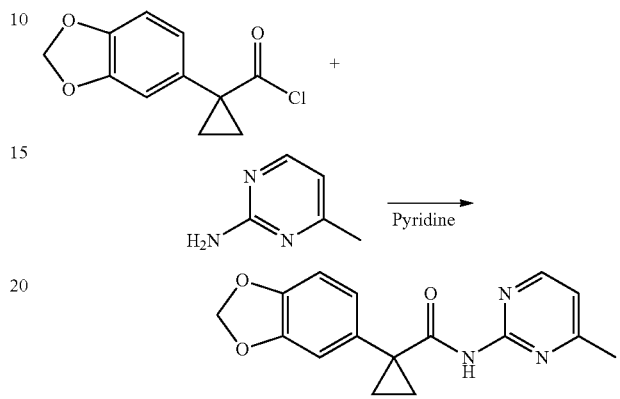

To 1-(benzo[d][1,3]dioxol-5-yl)cyclopropanecarbonyl chloride (45 mg, 0.2 mmol) in pyridine (2 mL) was added 4-methylpyrimidin-2-amine (22 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 297.3. Found 298.3 (M+1)⁺. Retention time 2.14 minutes.

Preparation of 1-(benzo[d][1,3]dioxol-5-yl)-N-(6-cyanopyridin-3-yl)cyclopropanecarboxamide

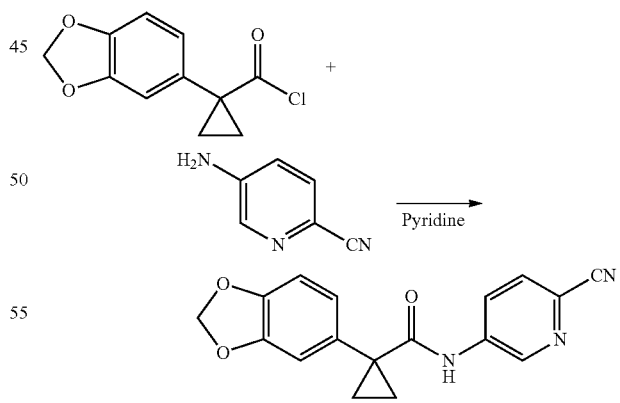

To 1-(benzo[d][1,3]dioxol-5-yl)cyclopropanecarbonyl chloride (45 mg, 0.2 mmol) in pyridine (2 mL) was added 5-aminopicolinonitrile (24 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 307.3. Found 308.3 (M+1)+. Retention time 2.87 minutes.

Preparation of 1-(benzo[d][1,3]dioxol-5-yl)-N-(2,6-dimethoxypyrimidin-4-yl)cyclopropanecarboxamide

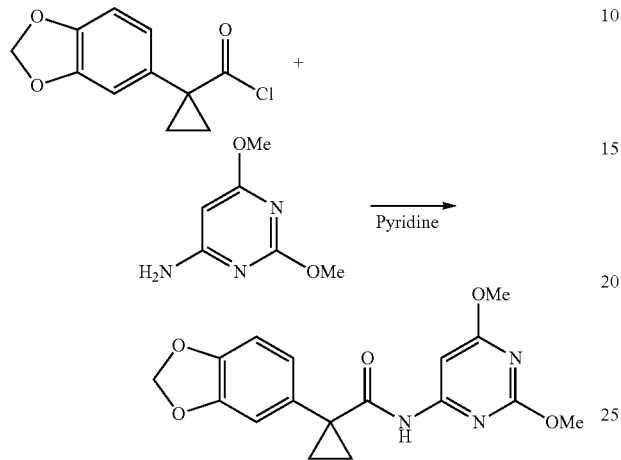

To 1-(benzo[d][1,3]dioxol-5-yl)cyclopropanecarbonyl chloride (45 mg, 0.2 mmol) in pyridine (2 mL) was added 2,6-dimethoxypyrimidin-4-amine (31 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 343.3. Found 344.1 (M+1)+. Retention time 2.87 minutes.

Preparation of 1-(benzo[d][1,3]dioxol-5-yl)-N-(6-(2,3-dimethylphenoxy)pyridin-3-yl)cyclopropanecarboxamide

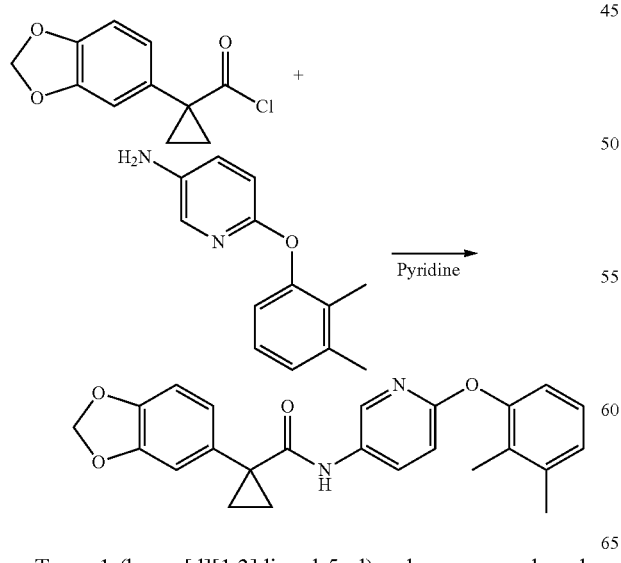

To 1-(benzo[d][1,3]dioxol-5-yl)cyclopropanecarbonyl chloride (45 mg, 0.2 mmol) in pyridine (2 mL) was added 6-(2,3-dimethylphenoxy)pyridin-3-amine (43 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 402.4. Found 403.1 (M+1)+. Retention time 3.11 minutes.

Preparation of 1-(benzo[d][1,3]dioxol-5-yl)-N-(4-(1-(4-chlorophenoxy)ethyl)pyrimidin-2-yl)cyclopropanecarboxamide

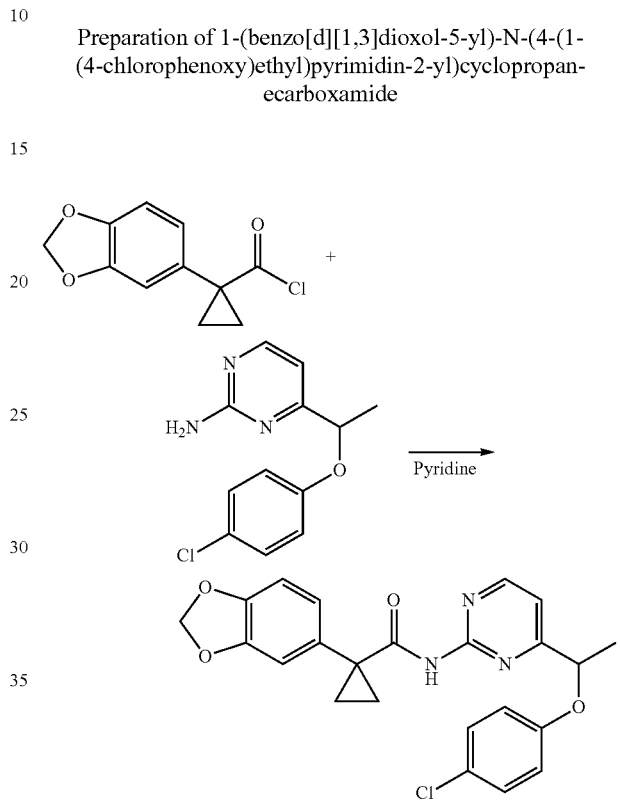

To 1-(benzo[d][1,3]dioxol-5-yl)cyclopropanecarbonyl chloride (45 mg, 0.2 mmol) in pyridine (2 mL) was added 4-(1-(4-chlorophenoxy)ethyl)pyrimidin-2-amine (50 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoracetic acid to yield the pure product. ESI-MS m/z calc. 437.9. Found 438.1 (M+1)+. Retention time 3.16 minutes.

Preparation of 1-(benzo[d][1,3]dioxol-5-yl)-N-(pyridin-2-yl)-N-(2-(trifluoromethyl)pyridin-4-yl)cyclopropanecarboxamide

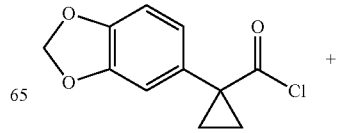

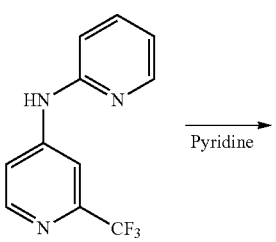

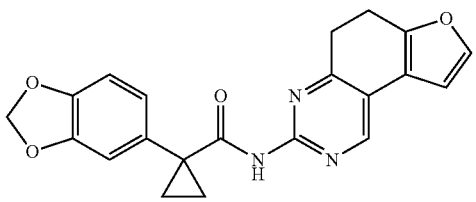

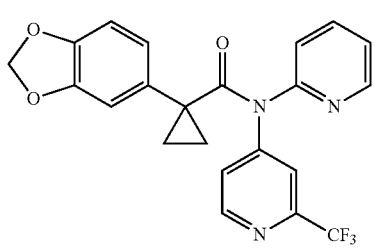

To 1-(benzo[d][1,3]dioxol-5-yl)cyclopropanecarbonyl chloride (45 mg, 0.2 mmol) in pyridine (2 mL) was added 5,6-dihydrofuro[3,2-f]quinazolin-3-amine (37 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoroacetic acid to yield the pure product. ESI-MS m/z calc. 375.4. Found 375.1 (M+1)$^+$. Retention time 2.61 minutes.

Preparation of 1-(benzo[d][1,3]dioxol-5-yl)-N-(2-tosylpyridin-3-yl)cyclopropanecarboxamide

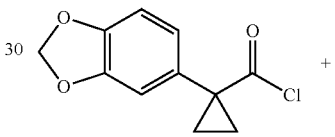

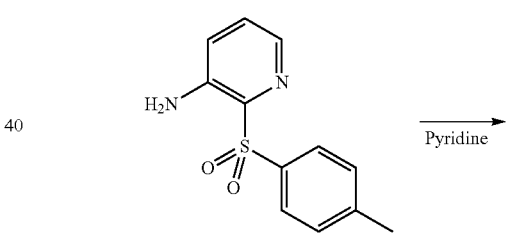

To 1-(benzo[d][1,3]dioxol-5-yl)cyclopropanecarbonyl chloride (45 mg, 0.2 mmol) in pyridine (2 mL) was added N-(2-(trifluoromethyl)pyridin-4-yl)pyridin-2-amine (48 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoroacetic acid to yield the pure product. ESI-MS m/z calc. 427.4. Found 428.1 (M+1)$^+$. Retention time 2.91 minutes.

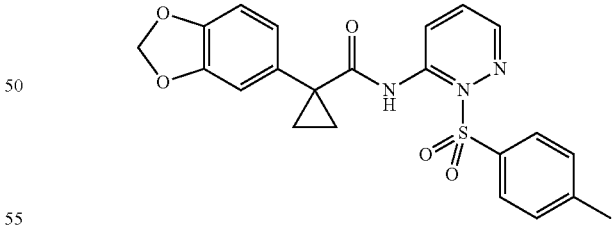

Preparation of 1-(benzo[d][1,3]dioxol-5-yl)-N-(5,6-dihydrofuro[2,3-h]quinazolin-2-yl)cyclopropanecarboxamide

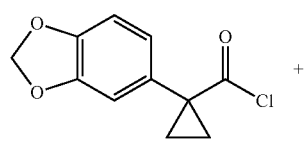

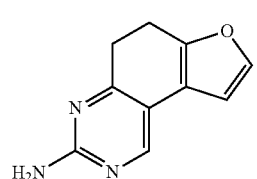

To 1-(benzo[d][1,3]dioxol-5-yl)cyclopropanecarbonyl chloride (45 mg, 0.2 mmol) in pyridine (2 mL) was added 2-tosylpyridin-3-amine (50 mg, 0.2 mmol) and the reaction mixture was stirred at 115° C. for 15 hours. The solvent was evaporated to dryness and the residue redissolved in DMF, filtered and purified by reverse-phase preparative liquid chromatography utilizing a gradient of 0-99% acetonitrile in water containing 0.05% trifluoroacetic acid to yield the pure product. ESI-MS m/z calc. 436.5. Found 437.1 (M+1)$^+$. Retention time 3.16 minutes.

Preparation of 3-(2-(1-(2,2-difluorobenzo[d][1,3]dioxol-5-yl)cyclopropanecarboxamido)-5-methylpyrimidin-4-yl)benzoic acid

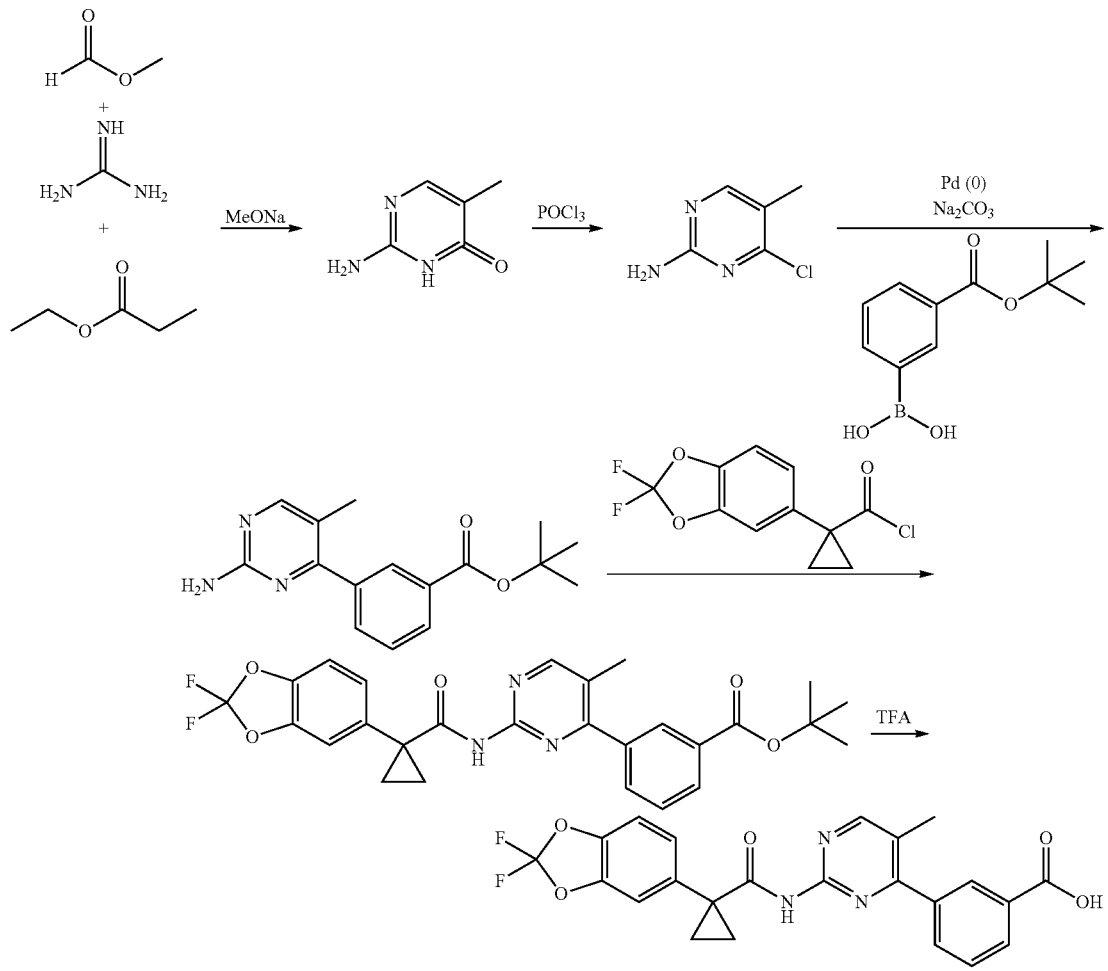

Step a: 5-Methylisocytosine

Freshly prepared sodium methoxide (10.8 g, 200 mmol) was suspended in a solution of ethyl propionate (15.3 g, 150 mmol) in DMF (20 mL) at room temperature. Methyl formate (6.0 g, 100 mmol) was added over a period of 1 hour. After stirring for 30 minutes, a solution of guanidine hydrochloride (9.6 g, 100 mmol) in MeOH (35 mL) was added rapidly and the reaction mixture was refluxed for 12 hours. After cooling to 30° C. and adjusting the pH to 6.0 with concentrated hydrochloric acid, the slurry was kept at 5° C. for 30 minutes. The solid was collected, washed with methanol, crystallized from water and dried in vacuo to give 5-methylisocytosine (7.3 g, 58.4% yield). $^1$H NMR (300 MHz, DMSO): δ10.83 (br s, 2 H), 7.38 (s, 1 H), 6.26 (br s, 2 H), 1.72 (s, 3 H).

Step b: 4-Chloro-2-amino-5-methylpyrimidine

A mixture of 5-methylisocytosine (3 g, 24.0 mmol) and POCl$_3$ (20 mL) was refluxed for 45 minutes. Excess of POCl$_3$ was removed under reduced pressure and the residue was poured over ice. The resulting mixture was made basic with ammonia at 10° C. The precipitate was filtrated and crystallized from ethanol to give 4-chloro-2-amino-5-methylpyrimidine (1 g 29.0% yield). $^1$H NMR (400 MHz, DMSO): δ 8.11 (s, 1 H), 6.81 (br s, 2 H), 2.04 (s, 3 H).

Step c: tert-Butyl 3-(2-amino-5-methylpyrimidin-4-yl)benzoate

To 4-chloro-5-methylpyrimidin-2-amine (150 mg, 1.04 mmol), tetrakistriphenylphosphine Palladium (0) (60 mg, 0.052 mmol) and 3-(tert-butoxycarbonyl)phenylboronic acid (347 mg, 1.56 mmol), 1,2-DME (3 mL) and Na$_2$CO$_3$ (1.04 mL, 2 M, 2.08 mmol) were added and heated to 120° C. in a microwave reactor for 30 minutes. The reaction mixture was filtered using EtOAc and the filtrate was dried over anhydrous Na$_2$SO$_4$ and evaporated under reduced pressure. The crude product was purified by column chromatography on silica gel to yield tert-butyl 3-(2-amino-5-methylpyrimidin-4-yl)benzoate (148 mg, 50%). ESI-MS m/z calc. 285.1. Found 286.5 (M+1)$^+$. Retention time 1.33 minutes.

Step d: tert-Butyl 3-(2-(1-(2,2-difluorobenzo[d][1,3]dioxol-5-yl)cyclopropanecarboxamido)-5-methylpyrimidin-4-yl)benzoate To 1-(2,2-difluorobenzo[d][1,3]dioxol-5-yl)cyclopropanecarbonyl chloride (91 mg, 0.35 mmol) and tert-butyl 3-(2-amino-5-methylpyrimidin-4-yl)benzoate (50 mg, 0.175 mmol), pyridine (2 mL) was added. The reaction was heated at 90° C. for twenty four hours. The pyridine was evaporated under reduced pressure. The resulting mixture was dissolved in ethyl acetate and filtered. The filtrate was washed with saturated aqueous NaHCO$_3$ (×3). The organic layer was dried over anhydrous Na$_2$SO$_4$ and evaporated under reduced pressure. The crude product was purified by column chromatography on silica gel to yield tert-butyl 3-(2-(1-(2,2-difluorobenzo[d][1,3]dioxol-5-yl)cyclopropanecarboxamido)-5-methylpyrimidin-4-yl)benzoate. ESI-MS m/z calc. 509.18. Found 510.5 (M+1)+. Retention time 2.22 minutes

Step e: 3-(2-(1-(2,2-Difluorobenzo[d][1,3]dioxol-5-yl)cyclopropanecarboxamido)-5-methylpyrimidin-4-yl)benzoic acid To tert-butyl 3-(2-(1-(2,2-difluorobenzo[d][1,3]dioxol-5-yl)cyclopropanecarboxamido)-5-methylpyrimidin-4-yl)benzoate (48 mg, 0.094 mmol) dicloromethane (1 mL) and TFA (726 µL) were added and stirred at room temperature for four hours. The dicloromethane and TFA were evaporated under reduced pressure. The crude product was dissolved in DMSO (1 mL), filtered and purified by reverse phase preparative HPLC to yield 3-(2-(1-(2,2-difluorobenzo[d][1,3]dioxol-5-yl)cyclopropanecarboxamido)-5-methylpyrimidin-4-yl)benzoic acid. ESI-MS m/z calc. 453.11. Found 454.3 (M+1)+. Retention time 1.63 minutes.

Preparation of 4-(2-(1-(2,2-difluorobenzo[d][1,3]dioxol-5-yl)cyclopropanecarboxamido)-5-methylpyrimidin-4-yl)benzoic acid

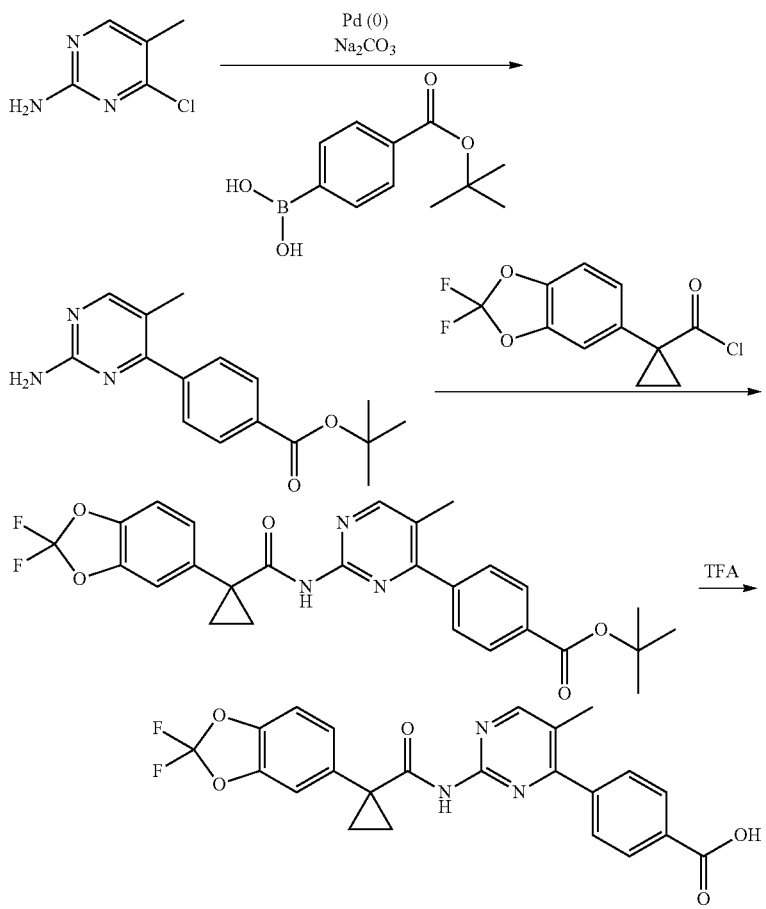

Step a: tert-Butyl 4-(2-amino-5-methylpyrimidin-4-yl)benzoate

To 4-chloro-5-methylpyrimidin-2-amine (150 mg, 1.04 mmol), tetrakistriphenylphosphine Palladium (0) (60 mg, 0.052 mmol) and 4-(tert-butoxycarbonyl)phenylboronic acid (347 mg, 1.56 mmol), 1,2-DME (3 mL) and Na$_2$CO$_3$ (1.04 mL, 2 M, 2.08 mmol) were added and heated to 120° C. in a microwave reactor for 30 minutes. The reaction mixture was filtered using EtOAc and the filtrate was dried over anhydrous Na$_2$SO$_4$ and evaporated under reduced pressure. The crude product was purified by column chromatography on silica gel to yield tert-butyl 4-(2-amino-5-methylpyrimidin-4-yl)benzoate (149 mg, 50%). ESI-MS m/z calc. 285.1. Found 286.3 (M+1)[+]. Retention time 1.36 minutes.

Step b: tert-Butyl 4-(2-(1-(2,2-difluorobenzo[d][1,3]dioxol-5-yl)cyclopropanecarboxamido)-5-methylpyrimidin-4-yl)benzoate To 1-(2,2-difluorobenzo[d][1,3]dioxol-5-yl)cyclopropanecarbonyl chloride (91 mg, 0.35 mmol) and tert-butyl 4-(2-amino-5-methylpyrimidin-4-yl)benzoate (50 mg, 0.175 mmol), pyridine (2 mL) was added. The reaction was heated at 90° C. for twenty four hours. The pyridine was evaporated under reduced pressure. The resulting mixture was dissolved in EtOAc and filtered. The filtrate was washed with saturated aqueous NaHCO₃ (×3). The organic layer was dried over anhydrous Na₂SO₄ and evaporated under reduced pressure. The crude product was purified by column chromatography on silica gel to yield tert-butyl 4-(2-(1-(2,2-difluorobenzo[d][1,3]dioxol-5-yl)cyclopropanecarboxamido)-5-methylpyrimidin-4-yl)benzoate. ESI-MS m/z calc. 509.2. Found 510.5 (M+1)⁺. Retention time 2.18 minutes.

Step c: 4-(2-(1-(2,2-Difluorobenzo[d][1,3]dioxol-5-yl)cyclopropanecarboxamido)-5-methylpyrimidin-4-yl)benzoic acid To tert-butyl 4-(2-(1-(2,2-difluorobenzo[d][1,3]dioxol-5-yl)cyclopropanecarboxamido)-5-methylpyrimidin-4-yl)benzoate (68 mg, 0.13 mmol) DCM (1.42 mL) and TFA (1.00 mL) were added and stirred at room temperature for one hour. The DCM and TFA were evaporated under reduced pressure. The crude product was dissolved in DMSO (1 mL), filtered and purified by reverse phase preparative HPLC to yield 4-(2-(1-(2,2-difluorobenzo[d][1,3]dioxol-5-yl)cyclopropanecarboxamido)-5-methylpyrimidin-4-yl)benzoic acid. ESI-MS m/z calc. 453.1. Found 454.3 (M+1)⁺. Retention time 1.62 minutes.

Preparation of 1-(2,2-difluorobenzo[d][1,3]dioxol-5-yl)-N-(4-(6-methoxypyridin-3-yl)-5-methylpyrimidin-2-yl)cyclopropanecarboxamide

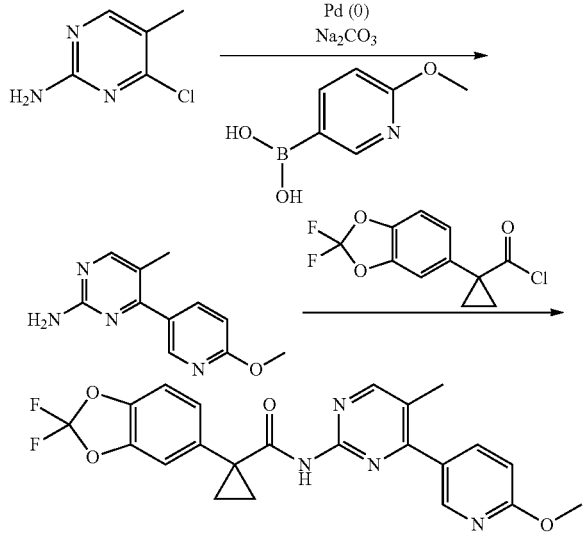

Step a: 4-(6-Methoxypyridin-3-yl)-5-methylpyrimidin-2-amine

To 4-chloro-5-methylpyrimidin-2-amine (250 mg, 1.74 mmol), tetrakistriphenylphosphine palladium (0) (100 mg, 0.087 mmol) and 6-methoxypyridin-3-ylboronic acid (398 mg, 2.60 mmol), 1,2-DME (6 mL) and Na₂CO₃ (1.74 mL, 2 M, 3.47 mmol) were added and heated to 120° C. in a microwave reactor for 30 minutes. The reaction mixture was filtered using acetonitrile and the filtrate was dried over anhydrous Na₂SO₄ and evaporated under reduced pressure. The crude product was purified by column chromatography on silica gel to yield 4-(6-methoxypyridin-3-yl)-5-methylpyrimidin-2-amine (160 mg, 43%). ESI-MS m/z calc. 216.10. Found 217.5 (M+1)+. Retention time 0.52 minutes.

Step b: 1-(2,2-difluorobenzo[d][1,3]dioxol-5-yl)-N-(4-(6-methoxypyridin-3-yl)-5-methylpyrimidin-2-yl)cyclopropanecarboxamide To 1-(2,2-difluorobenzo[d][1,3]dioxol-5-yl)cyclopropanecarbonyl chloride (369 mg, 1.42 mmol) and 4-(6-methoxypyridin-3-yl)-5-methylpyrimidin-2-amine (153 mg, 0.71 mmol), pyridine (4 mL) was added. The reaction was heated at 90° C. for three and a half hours. The pyridine was evaporated under reduced pressure. The resulting mixture was dissolved in ethyl acetate and filtered. The filtrate was washed with saturated aqueous NaHCO₃ (×3). The organic layer was dried over anhydrous Na₂SO₄ and evaporated under reduced pressure. The crude product was purified by column chromatography on silica gel to yield 1-(2,2-difluorobenzo[d][1,3]dioxol-5-yl)-N-(4-(6-methoxypyridin-3-yl)-5-methylpyrimidin-2-yl)cyclopropanecarboxamide. ESI-MS m/z calc. 440.13. Found 441.5 (M+1)+. Retention time 1.72 minutes.

Preparation of 1-(2,2-difluorobenzo[d][1,3]dioxol-5-yl)-N-(5-methyl-4-(6-oxo-1,6-dihydropyridin-3-yl)pyrimidin-2-yl)cyclopropanecarboxamide

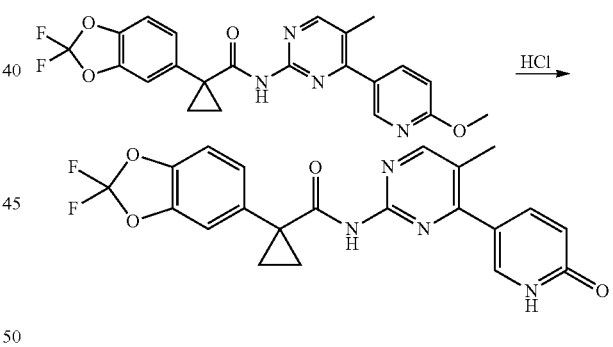

To a solution of 1-(2,2-difluorobenzo[d][1,3]dioxol-5-yl)-N-(4-(6-methoxypyridin-3-yl)-5-methylpyrimidin-2-yl)cyclopropanecarboxamide (126 mg, 0.286 mmol) in 1,4-dioxane (1.50 mL), 4 M aqueous HCl (775 μL, 3.10 mmol) was added and stirred at 90° C. for one hour. The reaction was cooled to room temperature, quenched with Et₃N and concentrated. The resulting mixture was dissolved in EtOAc and filtered. The solid was dissolved in water and the product was extracted using ethyl acetate (×3). The combined organic layers were dried over anhydrous Na₂SO₄ and evaporated under reduced pressure. The crude product was dissolved in DMSO (1 mL), filtered and purified by reverse phase preparative HPLC to yield 1-(2,2-difluorobenzo[d][1,3]dioxol-5-yl)-N-(5-methyl-4-(6-oxo-1,6-dihydropyridin-3-yl)pyrimidin-2-yl)cyclopropanecarboxamide. ESI-MS m/z calc. 426.11. Found 427.3 (M+1)+. Retention time 1.34 minutes.

Set forth below is the characterizing data for compounds of the present invention prepared according to the above examples.

TABLE 2

| Cmpd. No. | LC/MS M + 1 | LC/RT min. | NMR |
|---|---|---|---|
| 1 | 408.2 | 3.82 | |
| 2 | 405.3 | 3.61 | |
| 3 | 403 | 2.38 | |
| 4 | 404.3 | 3.34 | |
| 5 | 380.3 | 3.54 | |
| 6 | 480.2 | 1.87 | |
| 7 | 393.1 | 6.25 | |
| 8 | 480.2 | 1.91 | |
| 9 | 453.3 | 1.41 | H NMR (400 MHz, CD3CN) 8.68 (d, J = 6.7 Hz, 1 H), 8.52 (d, J = 6.7 Hz, 1 H), 8.21 – 8.18 (m, 1 H), 8.05 (d, J = 0.9 Hz, 1 H), 7.85 (s, 1 H), 7.68 – 7.67 (m, 2 H), 7.46 – 7.44 (m, 2 H), 7.29 (dd, J = 0.9, 7.8 Hz, 1 H), 1.75 – 1.73 (m, 5 H), 1.39 – 1.35 (m, 2 H) |
| 10 | 441.3 | 1.74 | |
| 11 | 454.3 | 1.62 | |
| 12 | 374.5 | 3.4 | |
| 13 | 408.5 | 3.49 | |
| 14 | 438.1 | 3.16 | |
| 15 | 308.3 | 2.87 | |
| 16 | 430.2 | 1.61 | |
| 17 | 416.2 | 1.56 | |
| 18 | 437.1 | 3.16 | |
| 19 | 373.1 | 2.44 | |
| 20 | 452.1 | 1.59 | |
| 21 | 270.1 | 2.47 | |
| 22 | 344.1 | 2.71 | |
| 23 | 376.1 | 2.61 | |
| 24 | 389.1 | 2.39 | |
| 25 | 298.3 | 2.14 | |
| 26 | 403.1 | 3.11 | |
| 27 | 374.1 | 3.32 | |
| 28 | 427.3 | 1.34 | |
| 29 | 403.2 | 1.54 | |
| 30 | 466.1 | 1.74 | |
| 31 | 325.3 | 2.14 | |
| 32 | 359.1 | 2.73 | |
| 33 | 404.5 | 3.37 | |
| 34 | 404.5 | 3.43 | |
| 35 | 314.1 | 2.31 | |
| 36 | 373.3 | 2.44 | |
| 37 | 407.5 | 2.67 | |
| 38 | 417.1 | 1.79 | |
| 39 | 416.2 | 1.51 | |
| 40 | 403.2 | 1.69 | |
| 41 | 428.1 | 2.91 | |
| 42 | 373.2 | 1.8 | |
| 43 | 404.5 | 2.29 | |
| 44 | 374.3 | 3.15 | |
| 45 | 454.3 | 1.63 | |
| 46 | 408.3 | 3.58 | |
| 47 | 403.3 | 2.5 | |

Assays for Detecting and Measuring ΔF508-CFTR Correction Properties of Compounds Membrane Potential Optical Methods for Assaying ΔF508-CFTR Modulation Properties of Compounds.

The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Correction Compounds

To identify small molecules that correct the trafficking defect associated with ΔF508-CFTR; a single-addition HTS assay format was developed. Assay Plates containing cells are incubated for ~2-4 hours in tissue culture incubator at 37° C., 5% $CO_2$, 90% humidity. Cells are then ready for compound exposure after adhering to the bottom of the assay plates.

The cells were incubated in serum-free medium for 16-24 hrs in tissue culture incubator at 37° C., 5% $CO_2$, 90% humidity in the presence or absence (negative control) of test compound. The cells were subsequently rinsed 3× with Krebs Ringers solution and loaded with a voltage sensing redistribution dye. To activate ΔF508-CFTR, 10 µM forskolin and the CFTR potentiator, genistein (20 µM), were added along with $Cl^-$-free medium to each well. The addition of $Cl^-$-free medium promoted $Cl^-$ efflux in response to ΔF508-CFTR activation and the resulting membrane depolarization was optically monitored using voltage sensor dyes.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a $Cl^-$ ion gradient in conjunction with channel activation with forskolin in a single liquid addition step using a fluoresecent plate reader such as FLIPR III after the cells have previously been treated with potentiator compounds (or DMSO vehicle control) and subsequently loaded with a redistribution dye.

Solutions:

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for Assaying ΔF508-CFTR Modulation Properties of Compounds.

1. Ussing Chamber Assay

Ussing chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM), PDE inhibitor, IBMX (100 μM) and CFTR potentiator, genistein (50 μM) were added to the apical side.

As observed in other cell types, incubation at low temperatures of FRT cells and human bronchial epithelial cells isolated from diseased CF patients (CF-HBE) expressing ΔF508-CFTR increases the functional density of CFTR in the plasma membrane. To determine the activity of correction compounds, the cells were incubated with test compound for 24-48 hours at 37° C. and were subsequently washed 3× prior to recording. The cAMP- and genistein-mediated $I_{SC}$ in compound-treated cells was normalized to 37° C. controls and expressed as percentage activity of CFTR activity in wt-HBE. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

2. Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, 10 EGTA, 10 HEPES, and 240 g/ml amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J- P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing <2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The compounds of Table 1 were found to exhibit Correction activity as measured in the assay described above.

Compounds of the invention are useful as modulators of ATP binding cassette transporters. Using the procedures described above, the activities, i.e., EC50s, of compounds of the present invention have been measured and are shown in Table 3.

TABLE 3

| IC50/EC50 Bins:+++ <= 2.0 < ++ <= 5.0 < + | | |
| PercentActivity Bins:+ <= 25.0 < ++ <= 100.0 < +++ | | |
| Cmpd. No. | BinnedEC50 | BinnedMaxEfficacy |
| --- | --- | --- |
| 1 | + | +++ |
| 2 | + | +++ |
| 3 | ++ | +++ |
| 4 | + | +++ |
| 5 | + | ++ |
| 6 | + | ++ |
| 7 | ++ | +++ |
| 8 | +++ | +++ |
| 9 | ++ | ++ |
| 10 | ++ | ++ |
| 11 | ++ | ++ |
| 12 | + | +++ |
| 13 | ++ | +++ |
| 14 | +++ | +++ |
| 15 | + | ++ |
| 16 | +++ | ++ |
| 17 | +++ | ++ |
| 18 | + | +++ |
| 19 | + | +++ |
| 20 | ++ | ++ |
| 21 | + | ++ |
| 22 | + | +++ |
| 23 | + | ++ |
| 24 | + | +++ |
| 25 | + | ++ |
| 26 | + | ++ |
| 27 | + | +++ |
| 28 | ++ | ++ |
| 29 | +++ | ++ |
| 30 | ++ | +++ |
| 31 | ++ | ++ |
| 32 | + | +++ |
| 33 | ++ | +++ |
| 34 | + | ++ |
| 35 | + | ++ |
| 36 | + | +++ |
| 37 | +++ | +++ |
| 38 | + | ++ |
| 39 | ++ | ++ |

TABLE 3-continued

| IC50/EC50 Bins:+++ <= 2.0 < ++ <= 5.0 < + | | |
| PercentActivity Bins:+ <= 25.0 < ++ <= 100.0 < +++ | | |
| Cmpd. No. | BinnedEC50 | BinnedMaxEfficacy |
| --- | --- | --- |
| 40 | ++ | +++ |
| 41 | + | ++ |
| 42 | ++ | +++ |
| 43 | ++ | +++ |
| 44 | ++ | ++ |
| 45 | ++ | ++ |
| 46 | ++ | ++ |
| 47 | ++ | ++ |

The invention claimed is:

1. A compound of formula I:

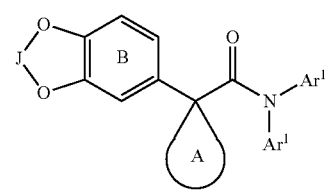

or a pharmaceutically acceptable salt thereof, wherein:
$Ar^1$ is

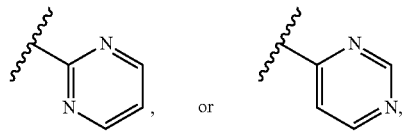 [SMILES: *c1ncccn1 ; *c1ccncn1]

$Ar^1$ is optionally substituted with w occurrences of —W—$R^W$; wherein
W is independently a bond or an optionally substituted (C1-C6) alkylidene chain wherein up to two methylene units of W are independently replaced by —CO—, —O—, —S—, —$SO_2$—, or —NR'—;
R' is independently H, alkyl, aryl, heteroaryl, aralkyl, cycloalkyl, or heterocycloalkyl; and
$R^W$ is independently H, halo, CN, $NO_2$, $NH_2$, $CF_3$, $OCF_3$, OH, alkoxy, or an optionally substituted aliphatic, cycloaliphatic, heterocyclic, aryl, or heteroaryl, wherein, when substituted, $R^w$ is substituted with up to two $R^2$;
$R^2$ is halo, CN, $NO_2$, $CF_3$, $OCF_3$, OR, —(C1-C6)alkylidene-OH, —(C1-C6)alkylidene-N(R)$_2$, OC(O)R, OC(O)N(R)$_2$, SR, S(O)R, $SO_2$R, $SO_2$N(R)$_2$, $SO_3$R, C(O)R, $CO_2$R, C(O)N(R)$_2$, N(R)$_2$, NRC(O)R, NRCO$_2$R, NRC(O)N(R)$_2$, NRSO$_2$R, B(OR)$_2$, or NRSO$_2$N(R)$_2$;
R is independently H, alkyl, cycloalkyl, heterocyclic, aryl, or heteroaryl;
$R^N$ is H, alkyl, aryl, heteroaryl, aralkyl, cycloalkyl, or heterocycloalkyl;
A is an optionally substituted 3-7 membered monocyclic ring;
B is optionally fused to a 5-7 membered ring selected from the group consisting of cycloaliphatic, aryl, heterocyclic, and heteroaryl;
J is selected from the group consisting of $CH_2$, $CF_2$, $C(CH_3)_2$, $C(O)$,

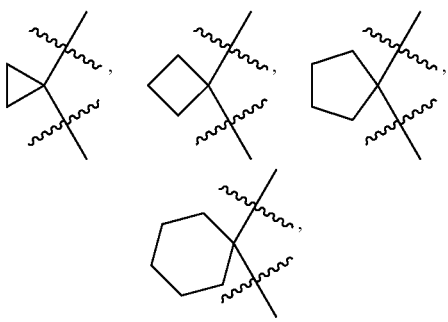

C(Phenyl)$_2$, B(OH), and CH(OEt); and
w is independently an integer from 0 to 5 inclusive.

2. The compound of claim 1, wherein A is

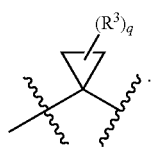

3. The compound of claim 1, wherein A is

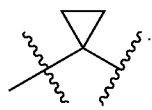 [SMILES: *C1(*)CC1]

4. The compound of claim 1, wherein J is CH$_2$.
5. The compound of claim 1, wherein J is CF$_2$.
6. The compound of claim 1, wherein R$^N$ is H.
7. The compound of claim 1, wherein optionally substituted Ar$^1$ is

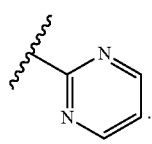 [SMILES: *c1ncccn1]

8. The compound of claim 1, wherein optionally substituted Ar$^1$ is

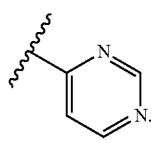

9. The compound of claim 1, wherein W is a bond.
10. The compound of claim 1, wherein W is an optionally substituted (C1-C6) alkylidene chain.
11. The compound of claim 1, wherein W is —CH$_2$—.
12. The compound of claim 1, wherein W is —NH—.
13. The compound of claim 1, wherein W is —O—.
14. The compound of claim 1, wherein W is —SO$_2$—.
15. The compound of claim 1, wherein R$^w$ is H.
16. The compound of claim 1, wherein R$^w$ is OH.
17. The compound of claim 1, wherein R$^w$ is aryl.
18. The compound of claim 1, wherein R$^w$ is phenyl.
19. The compound of claim 1, wherein R$^w$ is heteroaryl.
20. The compound of claim 1, wherein R$^w$ is pyridyl.
21. The compound of claim 1, wherein R$^w$ is alkoxy.
22. The compound of claim 1, wherein R$^w$ is methoxy.
23. The compound of claim 1, wherein R$^w$ is trifluoromethoxy.
24. The compound of claim 1, wherein R$^w$ is cycloalkyl.
25. The compound of claim 1, wherein R$^w$ is cyclohexyl.
26. The compound of claim 1, wherein R$^w$ is heterocycloalkyl.
27. The compound of claim 1, wherein R$^w$ is an unsaturated heterocycloalkyl.
28. The compound of claim 1, wherein R$^w$ is a pyridone.
29. The compound of claim 1, wherein R$^w$ is —(C1-C6)alkylidene-N(R)$_2$.
30. The compound of claim 1, wherein R$^w$ is —(C1-C6)alkylidene-OH.
31. The compound of claim 1, wherein R$^w$ is —CH$_2$OH.
32. The compound of claim 1, wherein Ar$^1$ is substituted with —W—R$^w$ that is an aryl, heteroaryl, or cycloalkyl ring.
33. The compound of claim 1, wherein Ar$^1$ is substituted with at least one —W—R$^w$ selected from the following:

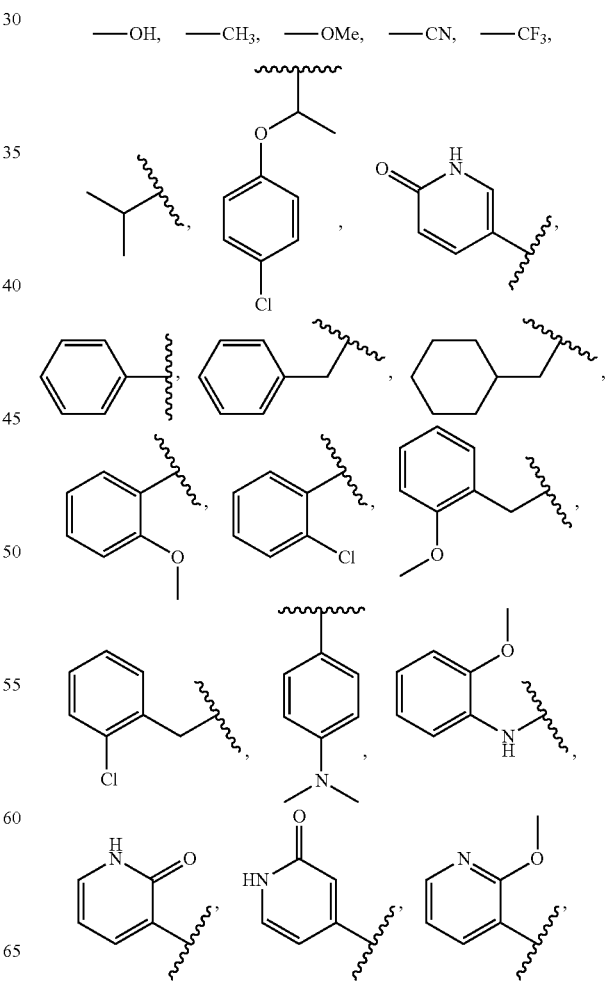

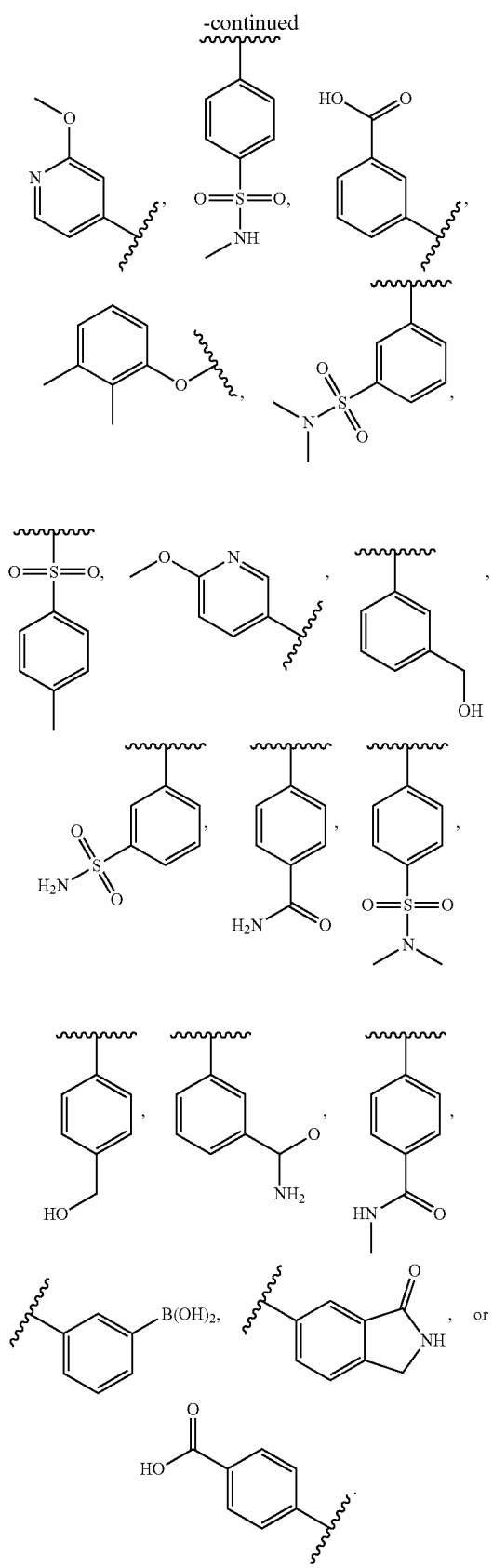
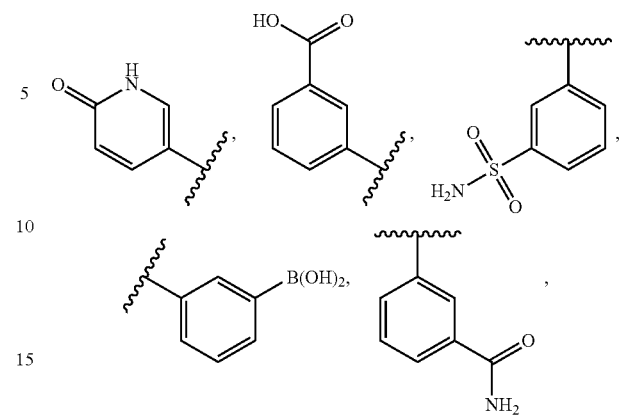
35. A compound selected from
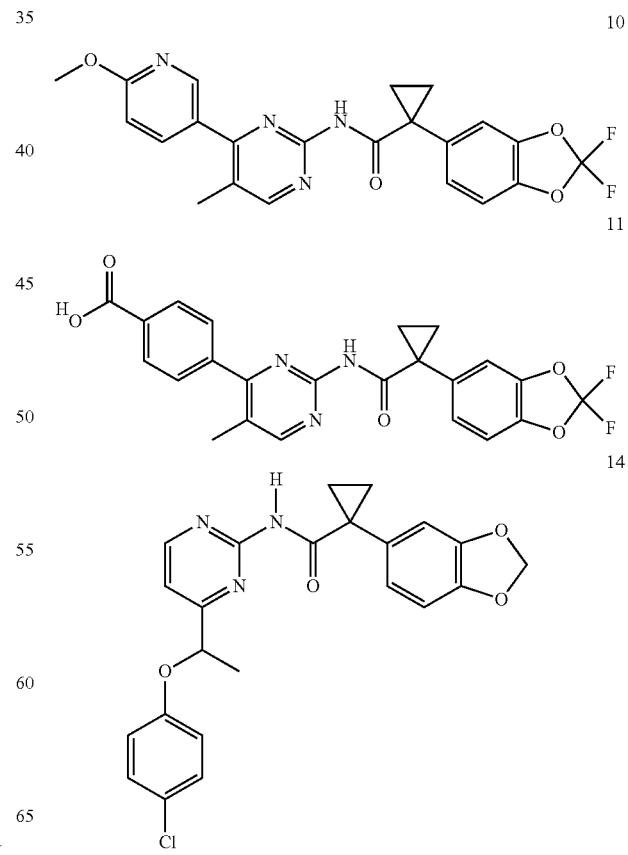
34. The compound of claim 1, wherein $Ar^1$ is substituted with at least one —W—$R^w$ selected from the following:

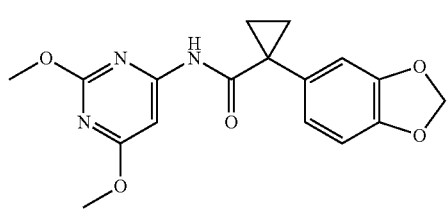

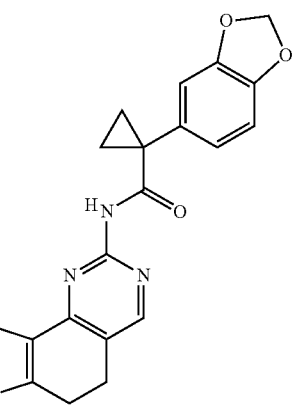

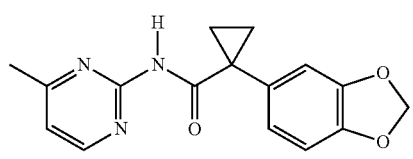

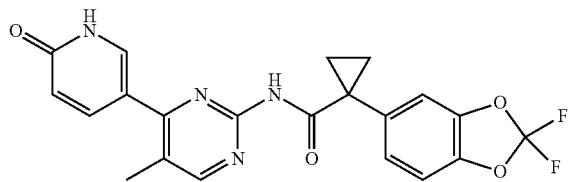

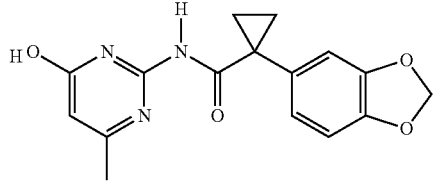

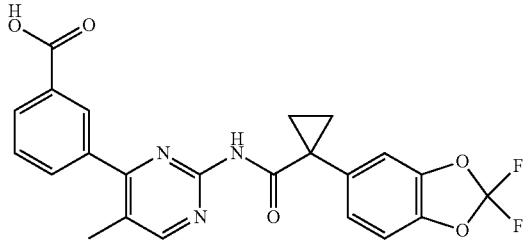

36. A pharmaceutical composition comprising
   (i) a compound of claim 1; and
   (ii) a pharmaceutically acceptable carrier.

37. The composition of claim 36, further comprising an additional agent selected from the group consisting of a mucolytic agent, bronchodialator, an anti-biotic, an anti-infective agent, an anti-inflammatory agent, CFTR corrector, and a nutritional agent.

38. A kit for use in measuring the activity of ΔF508-CFTR in a biological sample in vitro or in vivo, comprising:
   (i) a first composition comprising a compound according to claim 1; and
   (ii) instructions for:
      a) contacting the composition with the biological sample;
      b) measuring activity of said ABC transporter or a fragment thereof.

* * * * *